United States Patent
Carney et al.

(10) Patent No.: US 12,404,548 B2
(45) Date of Patent: Sep. 2, 2025

(54) INCREMENTAL SECONDARY ANALYSIS OF NUCLEIC ACID SEQUENCES

(71) Applicant: Illumina, Inc., San Diego, CA (US)

(72) Inventors: Michael J. Carney, San Diego, CA (US); Jacobus De Beer, San Diego, CA (US); Hsu-Lin Tsao, San Diego, CA (US); Partha Mukherjee, San Diego, CA (US); Daniel Joseph Tracy, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 1029 days.

(21) Appl. No.: 17/199,391

(22) Filed: Mar. 11, 2021

(65) Prior Publication Data
US 2021/0285043 A1    Sep. 16, 2021

Related U.S. Application Data

(60) Provisional application No. 62/988,374, filed on Mar. 11, 2020.

(51) Int. Cl.
*C12Q 1/6869* (2018.01)
*G06N 3/12* (2023.01)
*G16B 20/20* (2019.01)
*G16B 30/10* (2019.01)

(52) U.S. Cl.
CPC .......... *C12Q 1/6869* (2013.01); *G06N 3/12* (2013.01); *G16B 20/20* (2019.02); *G16B 30/10* (2019.02)

(58) Field of Classification Search
CPC ........ C12Q 1/6869; G06N 3/12; G16B 20/20; G16B 30/10; G16B 50/30
See application file for complete search history.

(56) References Cited

U.S. PATENT DOCUMENTS

| | | |
|---|---|---|
| 7,972,820 B2 | 7/2011 | Mayer |
| 9,679,104 B2 | 6/2017 | Van Rooyen et al. |
| 9,683,230 B2 | 6/2017 | Gormley et al. |
| 2015/0066385 A1 | 3/2015 | Schnall-Levin et al. |
| 2016/0180019 A1 | 6/2016 | Van Rooyen et al. |
| 2016/0306922 A1 | 10/2016 | Van Rooyen et al. |
| 2017/0342405 A1 | 11/2017 | Fu et al. |
| 2019/0172553 A1 * | 6/2019 | Wu ........................ G16B 20/00 |
| 2019/0259468 A1 | 8/2019 | Ojard |
| 2020/0372031 A1 | 11/2020 | Ruehle |

FOREIGN PATENT DOCUMENTS

| | | | | |
|---|---|---|---|---|
| WO | WO 2016/179437 | | 11/2016 | |
| WO | WO-2016179437 A1 * | | 11/2016 | ........... C12Q 1/6869 |
| WO | WO 2018/068014 | | 4/2018 | |
| WO | WO-2018068014 A1 * | | 4/2018 | ............... C12Q 1/68 |

OTHER PUBLICATIONS

Wikipedia 2024, Application-specific integrated circuit, https://en.wikipedia.org/wiki/Application-specific_integrated_circuit (Year: 2024).*
Wikipedia 2024, Field-programmable gate array, https://en.wikipedia.org/wiki/Field-programmable_gate_array (Year: 2024).*
PCT International Search Report and Written Opinion in International Appln. No. PCT/US2021/022012, dated Jul. 14, 2021, 19 pages.
CA Office Action in Canadian Appln. No. 3,167,358, mailed on Jan. 9, 2024, 7 pages.
PCT International Preliminary Report on Patentability in International Appln. No. PCT/US2021/022012, dated Sep. 6, 2022, 13 pages.
CA Office Action in Canadian Appln. No. 3,167,358, mailed on Oct. 22, 2024, 7 pages.

* cited by examiner

*Primary Examiner* — Olivia M. Wise
*Assistant Examiner* — Robert J. Kallal
(74) *Attorney, Agent, or Firm* — Heslin Rothenberg Farley & Mesiti P.C.

(57) ABSTRACT

Methods, systems, and apparatuses, including computer programs, for performing incremental secondary analysis of nucleic acid sequence reads. The method can include (i) obtaining first data describing a plurality of first reads generated by a nucleic acid sequencing device during a first read interval, (ii) obtaining second data describing a plurality of second reads generated by the nucleic acid sequencing device during a second read interval that is performed after the first read interval, wherein while the second data is being obtained: (a) providing, by the nucleic acid sequencing device, the first data as an input to a mapping and alignment unit, (b) receiving, from the mapping and alignment unit, alignment results, and (c) storing the received alignment results, and, thereafter (iii) instructing the mapping and alignment unit to begin alignment of the second data representing the second plurality of reads to the reference sequence.

35 Claims, 11 Drawing Sheets

INCREMENTAL SECONDARY ANALYSIS OF NUCLEIC ACID SEQUENCES

CROSS-REFERENCE TO RELATED APPLICATIONS

This application claims the benefit of U.S. Provisional Patent Application No. 62/988,374 filed Mar. 11, 2020, the entire contents of which is incorporated herein by reference in its entirety.

BACKGROUND

This disclosure relates to nucleic acid sequence analysis.

A nucleic acid sequencer is an instrument that is configured to automate the process of nucleic acid sequencing. Nucleic acid sequencing is a process of determining an order of nucleotides in a nucleic acid sequence. Nucleic acids may include deoxyribonucleic acid (DNA) or ribonucleic acid (RNA).

The nucleic acid sequencer is configured to receive a nucleic acid sample and generate output data, referred to as one or more "reads" that each represent an order of nucleotides in the nucleic acid sample. The nucleotides in a DNA sample can include one or more bases that include guanine (G), cytosine (C), adenine (A), and thymine (T) in any combination. The nucleotides in a RNA sample can include one or more bases that include G, C, A, and uracil (U) in any combination.

The reads generated by the DNA sequencer can be mapped to a known sequence of nucleotides of a reference genome using a mapping and aligning engine. The mapping of reads to a known sequence of nucleotides of the reference genome can be achieved by a mapping and aligning engine using a hash table index.

SUMMARY

The present disclosure is directed towards systems, methods, and computer programs for performing incremental secondary analysis. Incremental secondary analysis relates to the process of performing one or more secondary analysis operations on a nucleic acid read of a sample before nucleic acid sequencing of the sample is completed by a nucleic acid sequencer. The one or more secondary analysis operations can include nucleic acid read mapping, nucleic acid read aligning, variant calling, or any combination thereof.

According to one innovative aspect of the present disclosure, a method for performing incremental secondary analysis of nucleic acid sequence reads is disclosed. In one aspect, the method an include actions of (i) obtaining first data describing a plurality of first reads generated by a nucleic acid sequencing device during a first read interval, wherein each of the first reads represents a first ordered sequence of nucleotides, (ii) obtaining second data describing a plurality of second reads generated by the nucleic acid sequencing device during a second read interval that is performed after the first read interval, wherein each of the second reads represents a second ordered sequence of nucleotides, wherein while the second data is being obtained: (a) providing, by the nucleic acid sequencing device, the first data as an input to a mapping and alignment unit, (b) receiving, from the mapping and alignment unit, alignment results; and (c) storing the received alignment results, and, thereafter (iii) instructing the mapping and alignment unit to begin alignment of the second data representing the second plurality of reads to the reference sequence.

Other versions include corresponding systems, apparatus, and computer programs to perform the actions of methods defined by instructions encoded on computer readable storage devices.

These and other versions may optionally include one or more of the following features. For instance, in some implementations, at least a portion of the mapping and alignment unit is implemented using a programmable logic device.

In some implementations, the programmable circuit is a field programmable gate array (FPGA).

In some implementations, at least a portion of the mapping and alignment unit is implemented using an application specific integrated circuit (ASIC).

In some implementations, the mapping and alignment unit is included within the nucleic acid sequencing device.

In some implementations, one or more of the first reads includes data representing a first sample identifier, and one or more of the second reads includes data representing a second sample identifier.

In some implementations, the method can further include while the second data is being obtained: organizing the one or more first reads into respective groups based on at least a first sample identifier or a second sample identifier, and generating organization statistics, the organization statistics indicating a number of first reads corresponding to each sample identifier.

In some implementations, the method can further include providing output data that represents the stored alignment results corresponding to the plurality of first reads before or while aligning the second portion of the cluster of reads.

In some implementations, the method can further include instructing the mapping and alignment module to begin a subsequent alignment of the data representing the first plurality of reads to the reference sequence.

In some implementations, the method can further include while obtaining the second data, determining a set of likely variants for the first data representing the first plurality of reads that was aligned to the reference sequence.

In some implementations, the at least a portion of the second data representing the second plurality of reads is aligned while at least a different portion of second data representing the second plurality of reads is being obtained.

In some implementations, the mapping and alignment unit is instructed to begin alignment of the second data representing the second plurality of reads a predetermined number of sequencing cycles before the second data is completely obtained.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Nucleic acid sequencing of a biological sample by a nucleic acid sequencer is a time consuming and expensive task. Conventional systems have employed a linear workflow such as the linear workflow shown in FIG. 1A. Such conventional workflows linearly execute, in series, operations that include (i) primary analysis to generate nucleic acid sequencing reads, (ii) secondary analysis on the generated nucleic acid sequencing reads to generate aligned reads and variants, and in some instances, (iii) tertiary analysis using results of secondary analysis such as variants identified during variant calling. Tertiary analysis can include, for example, classification of identified variants, determining relevance of identified variants, determining a diagnosis based on identified variants, determining treatment based on the identified variants, or the like.

Figure 1A:
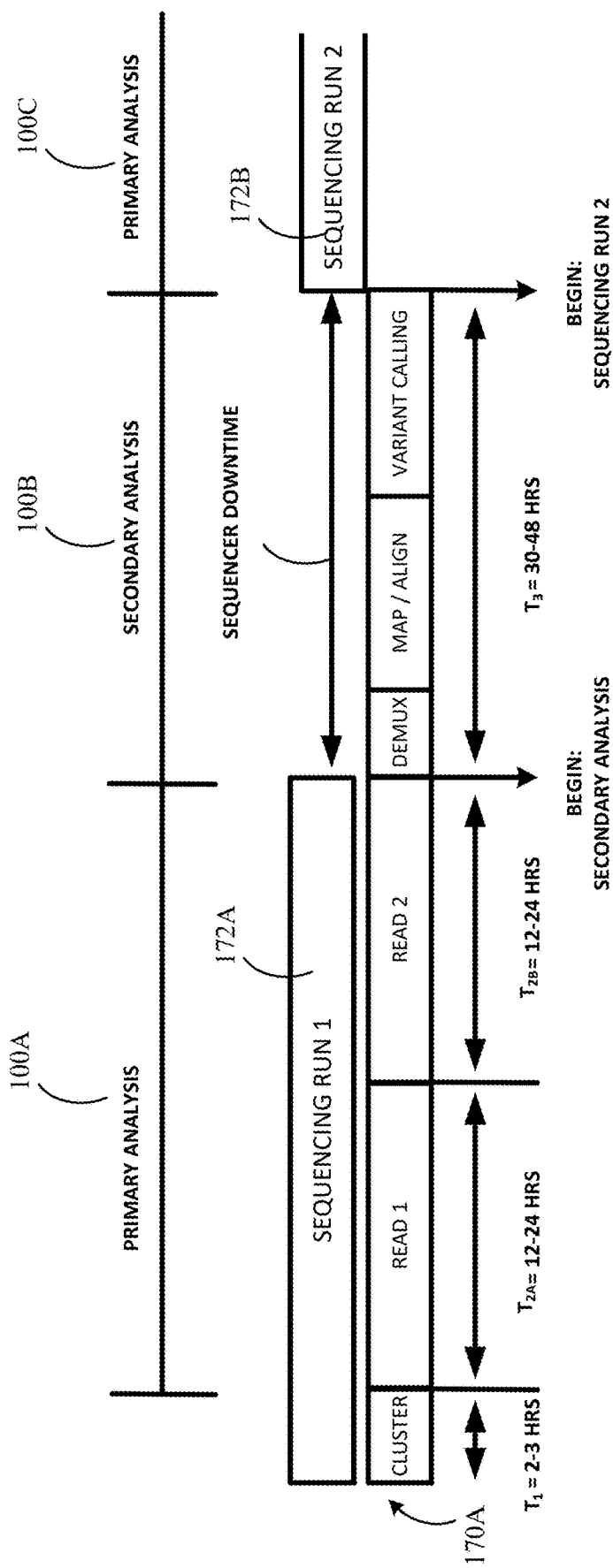
FIG. 1A is a schematic showing an example of a prior art workflow describing a linear sequence of secondary analysis operations.

With reference to FIG. 1A, a conventional workflow 170A is described that performs sequencing run 172A of one or more samples. The sequencing run 172A includes a clustering operation during time T1, a first read interval "Read 1" that includes sequencing operations to generate first reads of a sample during time T2A, and a second read interval "Read 2" that includes sequencing operations to generate second reads of the sample during another time T2B. During sequencing run 172A, a first primary analysis 100A processes data to generate the first and second reads. Primary analysis 100A can include, for example, the processing of images to generate the sequence of nucleotides or bases of each of the reads. After conclusion of the first primary analysis 100A, secondary analysis 100B begins. In this example of FIG. 1A, secondary analysis 100B is performed using software resources of a nucleic acid sequencer and includes demultiplexing the reads generated during primary analysis 100A of the first sequencing run 172A, mapping and aligning the demultiplexed reads, and then variant calling-all during time T3. It is only after the completion of secondary analysis that the next primary analysis 100C can be performed by a nucleic acid sequencer. Accordingly, by employing conventional workflows using conventional secondary analysis software by the nucleic acid sequencer, it takes at least TSUM=T1+T2A+T2B+T3—in some cases, approximately 56-99 hours—after initiating a first primary analysis 100A of a first sequencing run 172A until a second primary analysis 100C of a second sequencing run 172B can be performed. Moreover, this results in periods of sequencer downtime, where the sequencer is not performing secondary analysis and consuming reagents, in some cases at least 30-48 hours, thus reducing instrument throughput, the number of nucleotides processed in a given time interval, and negatively impacting revenue streams from reagent sales.

Conventional systems operate this way because conventional nucleic acid sequencers lack computational resources to run primary analysis and secondary analysis operations in parallel. Instead, software computing resources of the conventional nucleic acid sequencers are dedicated to sequencing operations during primary analysis and then these same computing resources are dedicated to demultiplexing, mapping, aligning, and variant calling operations during secondary analysis. In some implementations, demultiplexing can include sorting operations.

The present disclosure addresses these problems by offloading aspects of secondary analysis operations to a programmable logic unit having hardwired digital logic configured to perform one or more secondary analysis operations using hardware circuits. This drastically reduces the time-T3-required to perform secondary analysis operations. Moreover, the present disclosure parallelizes sequencing operations such as clustering, primary analysis, other sequencing operations, or a combination thereof, and secondary analysis as described herein to reduce overall processing time TSUM from the start of first sequencing run 172A to the start of second sequencing run 172B by modifying conventional nucleic acid sequencing devices to perform the parallelized workflow operations described herein.

Multiple other advantages are gained using the techniques of the present disclosure. First, the present disclosure can be used to conserve reagents used by a nucleic acid sequencer during sequencing runs. For example, by beginning secondary analysis operations during a sequencing run and completing at least a portion of the secondary analysis operations before sequencing is complete, the present disclosure can generate statistics such as alignment statistics, demultiplexing statistics, or the like, and evaluate the generated statistics to gauge a quality of reads generated during the primary analysis. If the statistics indicate that the quality of the reads generated by a nucleic acid sequencer are poor, then primary analysis can be terminated, the inputs to the sequencer can be reconfigured, and another sequencing run using the nucleic acid sequencer can be restarted. Thus, this process can save at least a portion of the reagent that would have been expended to complete the entire first primary analysis sequencing run by stopping the primary analysis sequencing run without using all of the reagent to complete a low quality sequencing run.

Second, the parallelized workflows of the present disclosure can enable tertiary analysis to begin sooner than conventional systems, thereby allowing certain diagnosis and treatments to be identified faster. For example, conventional workflows using conventional computing architectures can, in some cases, take up to a TSUM=approximately 56-99 hours before beginning tertiary analysis. However, in some implementations of the present disclosure, tertiary analysis can be started in as little as 2-12 hours or a few hours after sequencing is complete. In some instances, this can be particularly advantageous such as, e.g., providing a faster determination of whether symptoms of a patient are related to a virus or bacteria. However, multiple scenarios exist where determining a treatment in hours vs., in some cases, 3-4 days can provide a substantial benefit—e.g., enabling a patient an opportunity to be administered antibiotics (or other type of drug or treatment) before an infection (or other illness) causes irreversible damage.

These and other advantages will become apparent from the features described in the present disclosure.

Figure 1B:
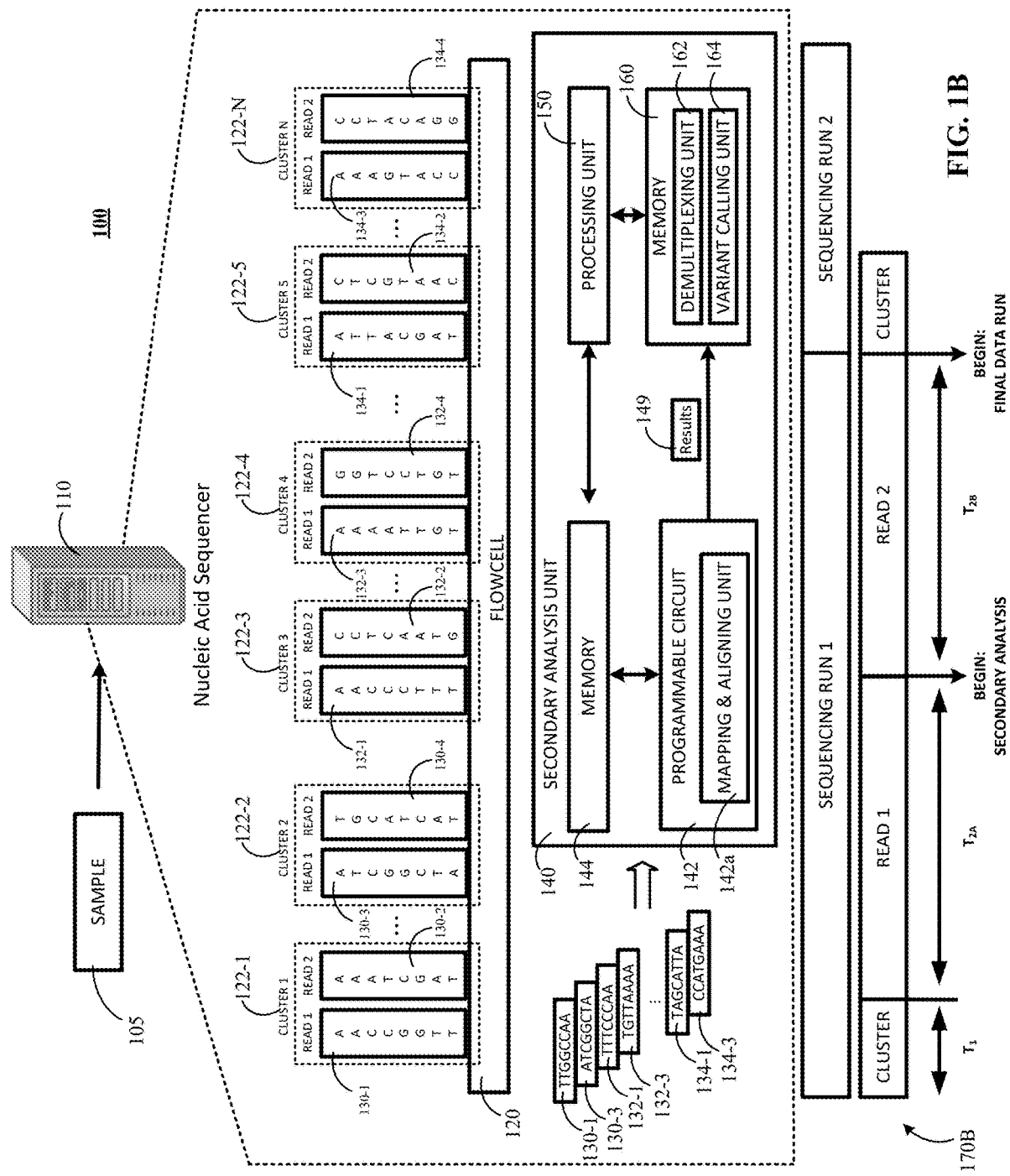
FIG. 1B is a contextual diagram of an example of a system for performing incremental secondary analysis on one or more samples using a secondary analysis unit located within a nucleic acid sequencer.

FIG. 1B is a contextual diagram of an example of a system 100 for performing incremental secondary analysis on one sample 105 using a secondary analysis unit 140 located within a nucleic acid sequencer. The system 100 includes a nucleic acid sequencer 110, one or more flow cells 120, one or more secondary analysis units 140, one or more processing units 150, and one or more memories 160. In the example of FIG. 1B, the secondary analysis unit 140 is located within the sequencer 110. However, the present disclosure is not so limited. Instead, the secondary analysis unit 140 can be located within one or more remote computers that are communicatively coupled to the sequencer 110 using one or more wired or wireless networks such as a LAN, a WAN, a cellular network, the Internet, or any combination thereof. The secondary analysis unit 140 can include the memory 140, the programmable circuit 142, the processing unit 150, the memory 160, or any combination thereof. For purposes of this specification, secondary analysis can include mapping operations, aligning operations, variant calling operations, or any subset or combination thereof. In some implementations, the processing unit 150, the memory 160, or both, may be used by the nucleic acid sequencer to perform other operations that are not related to secondary analysis.

The one or more processing units 150 of the nucleic acid sequencer 110 can include one or more processors configured to execute software instructions to realize functionality defined by the software instructions. For example, the one or more processing units 150 can obtain and execute software instructions defining a demultiplexing unit 162 stored in the memory 160 to realize the functionality of the demultiplexing unit 162. The one or more processing units 150 can include one or more central processing units (CPUs), one or more graphical processing units (GPUs), or any combination thereof.

The term "unit" is used in this specification to describe a software module, a hardware module, or a combination of both, that is used to perform a specified function. A determination of whether a particular "unit" described herein is hardware, software, or a combination of both, can be made based on the context of its use. For example, a "mapping and aligning unit" 142a resident in a programmable circuit 142 is a hardware unit whose functionality is realized by hardwired digital logic gates or hardwired digital logic blocks. By way of another example, a "demultiplexing unit" 162 resident in a memory 160 is a software unit whose functionality is realized by processing unit 150 executing software instructions defining the "demultiplexing unit" 162. By way of another example, the "processing unit" 150 is a hardware device that realizes functionality by processing software instructions, and thus functionality of the "processing unit" 150 is a combination of hardware and software. Similarly, the "secondary analysis unit" 140 can include a combination of hardware and software that is used to interact with the hardwired programmable circuit 142a.

The nucleic acid sequencer 110 is a device that is configured to perform sequencing operations such as primary analysis. Primary analysis can include receiving, by the nucleic acid sequencer 110, a biological sample 105 such as a blood sample, tissue sample, or sputum, and generating, by the nucleic acid sequencer 110, output data such as one or more reads 130-1, 130-2, 130-3, 130-4, 132-1, 132-2, 132-3, 132-4, 134-1, 134-2, 134-3, 134-4 that each represent an order of nucleotides of a nucleic acid sequence of the received biological sample. Sequencing, by the nucleic acid sequencer 110, can be performed in multiple read intervals, with a first read interval "Read 1" generating one or more first reads representing an order of nucleotides from a first portion, or end, of a nucleic acid sequence fragment (or strand) that has been clonally amplified into a clonal grouping of template nucleic acid fragments bound to a flowcell 120 and a second read interval "Read 2" generating one or more second reads respectively representing an order of nucleotides from a second portion, for example the other end, of the nucleic acid sequence fragment that has been clonally amplified into a clonal grouping of template nucleic acid fragments bound to a flowcell 120. Respective clonal groupings of template nucleic acid fragments bound to the flowcell 120 can be referred to herein as clusters such as cluster 1 122-1, cluster 2 122-2, cluster 3 122-3, cluster 4 122-4, cluster 5 122-5, cluster N 122-N.

As a result, during each read interval, a single read will be generated by the nucleic acid sequencing device 110 for each end of the nucleic acid fragment clonally amplified in a respective cluster. That is, the first read interval of a sequencing cycle will produce "Read 1" and the second read interval of a sequencing cycle will produce "Read 2." In some implementations, the nucleic acid sequence may sequence multiple clones of the nucleic acid fragment within the same cluster for imaging and determining or identifying the read sequence.

Thus, each read represents a portion of a particular nucleic acid sequence fragment. For example, assuming a short nucleic acid sequence fragment of approximately 600 nucleotides, a first read may represent 150 ordered nucleotides for the first end of the nucleic acid sequence fragment and a second read may represent 150 ordered nucleotides of the other end of the nucleic acid sequence fragment. These numbers, however, are merely examples and a nucleic acid sequencer 110 can be configured in a manner consistent with the spirit and scope of the present disclosure that generates short nucleic acid sequences and respective reads of different lengths than those mentioned here. A simple version of this concept is depicted with reference to FIGS. 1B, 3, and 5 to convey the principles of the present disclosure to a skilled artisan. Specifically, these figures depict reads, generated by a nucleic acid sequencer 110, of respective ends of clustered nucleic acid sequence fragments whose nucleic acid template was bound to a flow cell 120 and clonally amplified.

In some implementations, the biological sample can include a DNA sample and the nucleic acid sequencer 110 can process DNA. In such implementations, the order of sequenced nucleotides in a read 130-1, 130-2, 130-3, 130-4, 132-1, 132-2, 132-3, 132-4, 134-1, 134-2, 134-3, 134-4 generated by the nucleic acid sequencer can include one or more of guanine (G), cytosine (C), adenine (A), and thymine (T) in any combination. In other implementations, the nucleic acid sequencer 110 can process RNA, and the biological sample can include an RNA sample. In such RNA implementations, the order of sequenced nucleotides in a read generated by the nucleic acid sequencer can include one or more of G, C, A, and uracil (U) in any combination. Accordingly, though the example of FIG. 1B describes processing of a read comprised of G, C, A, and T that is based on a DNA sample, the present disclosure is not so limited. Instead, other implementations can process reads comprised of C, G, A, and U that are based on an RNA sample.

However, RNA sequencing does not require use of an RNA sequencer. For example, in some implementations nucleic acid sequencer 110 can be a DNA sequencer that sequences a sample and generated reads having one or more of G, C, A, and T. Then, in such implementations, nucleic acid sequencer 110 can transcribe the generated reads into cDNA to represent the RNA of the sequenced sample. In such implementations, the reads would be represented using bases that include G, C, A, and uracil (U) in any combination.

In some implementations, the nucleic acid sequencer 110 can include a next generation sequencer (NGS) that is configured to generate sequence reads such as reads 130-1, 130-2, 130-3, 130-4, 132-1, 132-2, 132-3, 132-4, 134-1, 134-2, 134-3, 134-4 for a given sample in a manner that achieves ultra-high throughput, scalability, and speed through the use of massively parallel sequencing technology. The NGS enables rapid sequencing of whole genomes, the ability to zoom into deeply sequenced target regions, utilize RNA sequencing (RNA-Seq) to discover novel RNA variants and splice sites, or quantify mRNAs for gene expression analysis, analysis of epigenetic factors such as genome-wide DNA methylation and DNA-protein interactions, sequencing of cancer samples to study rare somatic variants and tumor subclones, and studying of microbial diversity in humans or in the environment.

The process of generating the nucleic acid sequencing reads includes stages of sample preparation, cluster generation, and sequencing. The first stage includes sample preparation, which includes adding adapter sequences to the end of each DNA fragment. Through reduced cycle amplification, additional motifs are introduced such as any necessary indices that can be used to identify the sample from which the reads are derived and regions complimentary to flow cell 120 oligos. One or more examples of sample preparation on a solid support are described in U.S. Pat. No. 9,683,230, which is herein incorporated by reference in its entirety. The second stage includes clustering, where each DNA fragment is isothermally amplified, for example, using an amplification reagent. One or more examples of isothermal amplification of nucleic acids on a solid support are described in more detail in U.S. Pat. No. 7,972,820, which is herein incorporated by reference in its entirety. The flow cell 120 can include a glass slide with multiple lanes, with each lane including a lawn of two types of oligos. Hybridization is enabled by the first of two types of oligos to attach to its complementary oligos on the surface of the flow cell. A polymerase creates a complement of the hybridized fragment. The DNA fragments can be clonally amplified using a technique such as bridge amplification. In the implementation of system 100 and workflow 170B, the clustering stages occur during time T1 of workflow 170B. However, the present disclosure is not so limited. Instead, in some implementations, clustering may begin and be performed before time T1, performed off instrument, or both. In such implementations, time T1 can be removed from run time calculations and a sequencing run can begin at, e.g., T2A. Such pre-T1 and/or off instrument clustering can be implemented in systems 100 of FIG. 1, system 300 of FIG. 3, system 500 of FIG. 5, system 700 of FIG. 7, or any other implementation of the present disclosure. After bridge amplifications, reverse fragments are cleaved off, leaving only the forward fragments.

The third stage includes performance of sequencing operations during times T2A and T2B by the nucleic acid sequencer 110. During time T2A, the nucleic acid sequencer 110 performs X cycles of sequencing operations for a first read interval "Read 1" to generate a first read that corresponds to a first end of each respective nucleic acid sequence fragment clonally amplified in respective clusters 122-1, 122-2, 122-3, 122-4, 122-5, 122-N, where X and N can be any positive integer greater than zero. The first read of each DNA cluster includes a string of base calls corresponding to a portion of respective DNA associated with a particular cluster. For example the read 130-1 includes a string of base calls corresponding to a first end of the nucleic acid fragment associated with cluster 1 122-1, the read 130-3 includes a string of base calls corresponding to a first end of the nucleic acid fragment associated with cluster 2 122-2, the read 132-1 includes a string of base calls corresponding to a first end of the nucleic acid fragment associated with cluster 3 122-3, the read 132-3 includes a string of bases calls corresponding to a first end of the nucleic acid fragment associated with cluster 4 122-4, the read 134-1 includes a string of base calls corresponding to a first end of the nucleic acid fragment associated with cluster 5 122-5, and the read 134-3 includes a string of base calls corresponding to a first end of the nucleic acid fragment associated with cluster N 122-N. Each base call corresponds to or represents a nucleotide. These reads can be generated using a sequencing process such as sequencing by synthesis. Data representing the reads 130-1, 130-3, 132-1, 132-3, 134-1, and 134-3 can be output to a memory 160 of the nucleic acid sequencer 110, input to memory 144 of the secondary analysis unit 140, or both.

In the implementation of system 100 and FIG. 1B, these first reads 130-1, 130-3, 132-1, 132-3, 134-1, and 134-3 sequenced during time T2A of a first read interval of workflow 170B represent a number of nucleotides on the first end of a DNA fragment associated with each cluster. For example, in some implementations a DNA fragment sequenced by nucleic acid sequencer 110 may include 600 nucleotides. The first reads 130-1, 130-3, 132-1, 132-3, 134-1, and 134-3 cluster may represent, e.g., a first 150 nucleotides of a first end of the 600 nucleotide DNA fragment amplified in the respective cluster. Each read interval is a massively parallel process that sequences hundreds of millions of clusters of DNA fragments simultaneously. Once the first read interval is completed at the end of T2A, the nucleic acid sequencer 110 can initiate a second read interval during time T2B that sequences the opposite end of each DNA fragment in each cluster to generate second reads 130-2, 130-4, 132-2, 132-4, 134-2, 134-4. By way of example the read 130-2 includes a string of base calls corresponding to a second end of the nucleic acid fragment associated with cluster 1 122-1, the read 130-4 includes a string of base calls corresponding to a second end of the nucleic acid fragment associated with cluster 2 122-2, the read 132-2 includes a string of base calls corresponding to a second end of the nucleic acid fragment associated with cluster 3 122-3, the read 132-4 includes a string of base calls corresponding to a second end of the nucleic acid fragment associated with cluster 4 122-4, the read 134-2 includes a string of base calls corresponding to a second end of the nucleic acid fragment associated with cluster 5 122-5, and the read 134-4 includes a string of base calls corresponding to a second end of the nucleic acid fragment associated with cluster N 122-N. In this implementation of system 100 and FIG. 1, the second read interval begins at approximately Time=T1+T2A of workflow 170B.

In conventional systems, as described with reference to FIG. 1A, secondary analysis operations such as mapping and aligning of the first reads 130-1, 130-3, 132-1, 132-3, 134-1, and 134-3 would not occur until after the end of the second read interval "Read 2" at the end of Time=T1+T2A+T2B. However, the system 100 of FIG. 1B as described by the present disclosure is configured to initiate secondary analysis operations of the first reads 130-1, 130-3, 132-1, 132-3, 134-1, 134-3 at Time=T1+T2A, with the secondary analysis of the first reads 130-1, 130-3, 132-1, 132-3, 134-1, 134-3 beginning, and occurring, during the second read interval "Read 2" while the nucleic acid sequencer 110 is performing sequencing operations of the second read interval "Read 2" to generate the second reads 130-2, 130-4, 132-2, 132-4, 134-2, 134-4.

The system 100 achieves this parallel processing advantage by offloading secondary analysis operations of the first reads to the secondary analysis unit's 140 programmable circuit 142a. Offloading secondary analysis operations to the secondary analysis unit 140 frees up processing unit 150, memory 160, or both, of the nucleic acid sequencer 110 to continue performance of primary analysis operations of the second read interval "Read 2" to generate second reads 130-2, 130-4, 132-2, 132-4, 134-2, 134-4 by sequencing the opposite end of the DNA cluster while secondary analysis of one or more of the first reads is being performed. Accordingly, the present disclosure enables sequencing operations such as primary analysis to be done in parallel with one or more secondary analysis operations.

The secondary analysis unit 140 includes a programmable circuit 142 that can be dynamically configured to include one or more secondary analysis operational units such as a mapping and aligning unit 142a to perform one or more secondary analysis operations. Dynamically configuring the programmable circuit 142 to include a secondary analysis operational unit such as a mapping and aligning unit 142a can include, for example, providing one or more instructions to the programmable circuit 142 that causes the programmable circuit 142 to arrange hardware logic gates of the programmable circuit 142 into a hardwired digital logic configuration that is configured to realize functionality, in hardware logic, of the mapping and aligning unit 142a. The hardware logic gates of the programmable circuit 142 may be realized using compiled hardware description language code or the like. Initial configurations of the programmable circuit 142 and subsequent reconfiguration of the programmable circuit 142 can be initiated by execution of software triggers that are satisfied by the nucleic acid sequencer 110 or other computer hosting the programmable circuit 142. For example, in the implementation of system 100 of FIG. 1B, at the end of Read 1 interval cycle, the nucleic acid sequencer 110 or other computer hosting the programmable circuit 142 can execute software instructions that trigger reconfiguration of the programmable circuit to performing mapping and aligning operations. Such execution of the aforementioned software triggers can, for example, cause loading of compiled hardware description language code into a memory of the programmable circuit 142 that can be executed by a programmable circuit control and cause reconfiguration of the programmable circuit 142 logic gates. Configured functionality of the mapping and aligning unit 142a can include obtaining one or more reads such as first reads 130-1, 130-3, 1S32-1, 132-3, 134-1, 134-3, mapping the obtained first reads 130-1, 130-3, 132-1, 132-3, 134-1, 134-3 to one or more reference sequence locations, and then aligning the mapped first reads 130-1, 130-3, 132-1, 132-3, 134-1, 134-3 to the one or more reference sequence locations. A reference sequence can include an organized series of nucleotides corresponding to a known genome.

Arranging hardware logic gates of the programmable circuit 142, responsive to the one or more instructions, can include configuring logic gates such as AND gates, OR gates, NOR gates, XOR gates, or any combination thereof, to execute digital logic functions of a mapping and aligning unit 142a. Examples of use of a programmable logic circuit such as an FPGA to perform functions of mapping and aligning unit are described in more detail, for example, by U.S. Pat. No. 9,679,104 or U.S. Pub. No. 2020/0372031, each of which are hereby incorporated by reference in their entirety. Alternatively, or in addition, arranging hardware logic gates can include dynamically configured logic blocks comprising customizable hardware logic units to perform complex computing operations including addition, multiplication, comparisons, or the like. The precise arrangement of the hardware logic gates, logic blocks, or a combination thereof, is defined by the received instructions. The received instructions can include, or are derived from, compiled hardware description language (HDL) program code that was written by an entity and defines the schematic layout of the secondary analysis operational unit that is to be programmed. The HDL program code can include program code written in a language such a Very High Speed Integrated Circuit Hardware Description Language (VHDL), Verilog, or the like. The entity can include one or more human users that drafted the HDL program code, one or more artificially intelligent agents that generated the HDL program code, or a combination thereof.

In some implementations, the programmable circuit 142 can include one or more field programmable gate arrays (FPGA), complex programmable logic devices (CPLD), or a programmable logic arrays (PLA), or a combination thereof, that are dynamically configurable and reconfigurable, as needed, by the nucleic acid sequencer 110 to execute a particular workflow. For example, in some implementations, it may be desirable to use the programmable logic circuit 142 as a mapping and aligning unit 142a, as described above. However, in other implementations, it may be desirable to use the programmable circuit 142 to perform variant calling functions or functions in support of variant calling such as a Hidden Markov Model (HMM) unit. In yet other implementations, the programmable circuit 142 can also be dynamically configured to support general computing tasks such as compression and decompression, as the hardware logic of the programmable circuit 142 is capable of performing these tasks, and the other tasks identified above, much faster than the performance of the same tasks using software instructions executed by one or more processing units 150.

Programmable circuits 142 are an example of one type of integrated circuit can provide the advantages of present disclosure described herein. However, other types of integrated circuits can be used as hardwired digital logic of the secondary analysis unit 140 that can offload secondary analysis of the nucleic acid sequencer 110 to free up resources of the nucleic acid sequencer 110 for primary analysis. For example, in some implementations, a secondary analysis unit 140 can be configured to use one or more Application-Specific Integrated Circuits (ASIC). Though not reprogrammable, one or more ASICs can be designed with custom hardware logic of one or more secondary analysis operational units such as a mapping and aligning unit, a variant calling unit, a variant calling computational support unit, or the like to accelerate and parallelize performance secondary analysis operations. In some implementations, use of the ASICs as the hardwired logic circuits of the secondary analysis unit 140 that realizes functionality of one or more secondary analysis operations units can be even faster than using a programmable circuit. Accordingly, a skilled artisan would understand that an ASIC could be used in place of the FPGA in any of the embodiments described herein.

By way of example, in some implementations, the programmable logic circuit 142 can be implemented using an FPGA that be dynamically configured as a decompression unit to access data representing the first reads 130-1, 130-3, 132-1, 132-3, 134-1, 134-3 received from the nucleic acid sequencer and decompress the data representing the first reads (e.g., if the reads received from the nucleic acid sequencer are compressed). The decompression unit can store decompressed reads stored in the memory 144 or 160. In such implementations, the FPGA can then be dynamically reconfigured as a mapping and aligning unit 142a to perform mapping and aligning of the decompressed first reads stored in the memory 144 or 160. The mapping and aligning unit 142a can then store data representing the mapped and aligned reads in the memory 144 or 160. Next, the FGPA can be dynamically reconfigured into variant calling unit or unit configured to perform functions in support of a software variant calling unit (e.g., HMM unit) and perform variant calling operations to generate output data that can be used by the sequencing system 100 to generate a Variant Calling Format (VCF) file based on the stored data representing the mapped and aligned reads. The high execution speed of these hardware modules executed using the FPGA can reduce secondary analysis of reads from 30 to 48 hours of conventional methods to being performed in a matter of minutes. Though a series of operations is described as including decompression, mapping and aligning, and variant calling operations is described, the present disclosure is not limited to performing all of those operations. Instead, the programmable circuit 142 can be dynamically configured to perform any operational unit in any order, as necessary, to parallelize secondary analysis offloaded from the nucleic acid sequencer 110.

With reference to the example of FIG. 1A, the nucleic acid sequencer 110 can configure the programmable circuit 142 of the secondary analysis unit 140 to include a mapping and alignment unit 142a. The nucleic acid sequencer 110 can receive a sample 105 such as nucleic acid of an entity such as a human person, non-human animal, or plant. The nucleic acid sequencer 110 can prepare the sample 105 and perform cluster generation during time T1 of the workflow 170B. The nucleic acid sequencer 110 can perform sequencing operations such as sequencing-by-synthesis during a first read interval to generate first reads 130-1, 130-3, 132-1, 132-3, 134-1, 134-3 during a time T2A that occurs following time T1. At the end of time T1+T2A, the nucleic acid sequencer 110 completes sequencing of the first reads 130-1, 130-3, 132-1, 132-3, 134-1, 134-3 and begins sequencing of the second reads 130-2, 130-4, 132-2, 132-4, 134-2, 134-4.

The nucleic acid sequencer 110 is configured to parallelize secondary analysis operations such as mapping and aligning of the first reads 130-1, 130-3, 132-1, 132-3, 134-1, 134-3 with sequencing operations such as sequencing-by-synthesis of a second read interval to generate second reads 130-2, 130-4, 132-2, 132-4, 134-2, 134-4 during the time period T2B. The mapping and aligning unit 142a can generate mapping and aligning results 149 and store the mapping and aligning results in the memory 160 of nucleic acid sequencer 110, the memory 144, some other memory that is accessible to the nucleic acid sequencer 110, some other memory that is accessible to a user of the nucleic acid sequencer 110, or a combination thereof. The results 149 can include data describing mapping and aligning statistics such as, for example, a Mapping Quality (MAPQ) score that provides an indication of mapping quality, an alignment score that provides an indication of alignment quality, or the like.

In the example of FIG. 1A, the ultrafast execution times of the mapping and aligning unit 142a implemented using hardwired digital logic of the programmable circuit 142 enables the mapping and aligning unit 142a to perform mapping and aligning of the first reads 130-1, 130-3, 132-1, 132-3, 134-1, 134-3 in a fraction of the time that is required, by the nucleic acid sequencer 110, to perform the second read interval. For example, in some implementations, the programmable circuit 142 can perform mapping and aligning of the first reads 130-1, 130-3, 132-1, 132-3, 134-1, 134-3 in mere minutes while sequencing of the second reads 130-2, 130-4, 132-2, 132-4, 134-2, 134-4 can take 12 to 24 hours. Accordingly, the mapping and aligning results 149 can be evaluated by the nucleic acid sequencer 110, a user of the nucleic acid sequencer 110, or both, and a determination can made, based on the quality of the mapping and alignment of the first reads 130-1, 130-3, 132-1, 132-3, 134-1, 134-3 as indicated by the mapping and alignment statistics whether the nucleic acid sequencer 110 should continue sequencing the second reads 130-2, 130-4, 132-2, 132-4, 134-2, 134-4.

This determination as to whether sequencing of the second reads 130-2, 130-4, 132-2, 132-4, 134-2, 134-4 should continue can be made automatically by the nucleic acids sequencer 110, manually by a user of the nucleic acid sequencer 110, or based on data describing a determination from both. By way of example, the nucleic acid sequencer 110 can be configured to determine whether mapping and aligning statistics such as alignment scores for the first reads 130-1, 130-3, 132-1, 132-3, 134-1, and 134-3 satisfy a predetermined threshold. If one or more alignment scores satisfy the predetermined threshold, then the nucleic acid sequencer 110 can continue sequencing the second reads 130-2, 130-4, 132-2, 132-4, 134-2, 134-4. Alternatively, if it is determined that the one or more alignment scores do not satisfy the predetermined threshold, then the nucleic acid sequencer 110 can terminate sequencing of the second reads 130-2, 130-4, 132-2, 132-4, 134-2, 134-4.

By way of a different example, in some implementations, the mapping and aligning results 149 can be manually reviewed by a user of the nucleic acid sequencer 110. In such instances, a user can determine whether the nucleic acid sequencer 110 is to continue sequencing the second reads 130-2, 130-4, 132-2, 132-4, 134-2, 134-4 based on the quality of the alignment of the first reads 130-1, 130-3, 132-1, 132-3, 134-1, 134-3 as indicated by the alignment scores.

By way of yet another example, determinations can be made by both the nucleic acid sequencer 110 and the user as to whether sequencing of the second reads should continue based on the quality of the alignment of first reads indicated by alignment scores indicated by the mapping and aligning results 149. In such implementations, data describing the determinations of the nucleic acid sequencer 110 and the user can be obtained, and in some implementations, the nucleic acid sequencer 110 will only terminate the second read interval if both the nucleic acid sequencer 110 and the user agree that the second read interval should be terminated.

In yet other implementations, a weighted average of the two determinations can be computed to produce an aggregate score representing a determination of both the nucleic acid sequencer 110 and the user. In such implementations, the nucleic acid sequencer 110 may only terminate if the aggregate score fails to satisfy a predetermined quality threshold. In yet other implementations, data representing the alignment statistics, data representing a user determination as to whether sequencing of a second read interval should continue, data representing one or more of the first reads, other data such as data representing features of the sample 105, or a combination thereof, can be vectorized and input to an artificially intelligent agent such as a machine learning model that has been trained to determine whether a nucleic acid sequencer 110 should continue primary analysis of a second read interval. In such implementations, the machine learning model can be previously trained based on labeled training data tagged as "terminate second read interval" or "continue with second read interval," or their respective equivalents. The labeled training data can include data representing the same input types that will be provided to the machine learning model at runtime. Such input types can include data representing the alignment statistics, data representing a user determination as to whether sequencing of a second read interval should continue, data representing one or more of the first reads, other data such as data representing features of the sample 105, or a combination thereof.

Using the mapping and aligning results 149 generated based on the mapping and aligning of the first reads 130-1, 130-3, 132-1, 132-3, 134-1, 134-3 to one or more reference sequences enables the conservation of reagent used, by the nucleic acid sequencer 110, during the second read interval to generate second reads 130-2, 130-4, 132-2, 132-4, 134-2, 134-4. For instance, poor alignment scores for the first reads 130-1, 130-3, 132-1, 132-3, 134-1, 134-3 can indicate the existence of a number of problems such as a contaminated sample 105, sequencing errors, a combination thereof, or the like. Accordingly, in such instances, rather than use reagents, which can be very expensive, to sequence the second reads during the second read interval and further delay the time it takes to begin running another round of primary analysis, the nucleic acid sequencer 110 can be shut down, reconfigured, and then used to begin primary analysis of another sample in a fraction of the time it would have taken to let the nucleic acid sequencer 110 finish its low quality sequencing run. In some implementations, once a determination as been made that the quality of mapping and alignment of the first reads is satisfactory, the nucleic acid sequencer 110 can discard the mapping and aligning results 149. In other implementations, the mapping and alignment of the first reads performed in parallel with the second read interval can be used as the mapping and alignment results for a final data run of the first reads.

Continuing with the example of FIG. 1B, after it has determined that the mapping and alignment results are satisfactory, the nucleic acid sequencer 110 can continue execution of the second read interval to generate the second reads. Once the second reads 130-2, 130-4, 132-2, 132-4, 134-2, 134-4 are generated, the nucleic acid sequencer 110 can instruct the secondary analysis unit 140 to begin its final secondary analysis data run. The final secondary analysis data run can include mapping and aligning the first reads 130-1, 130-3, 132-1, 132-3, 134-1, 134-3 and the second reads 130-2, 130-4, 132-2, 132-4, 134-2, 134-4 using the secondary analysis unit 140. Because these secondary analysis operations are implemented using the programmable circuit 142a, these secondary analysis operations can be performed in parallel with a second sequencing run and in a fraction of the time required to perform the second sequencing run.

This provides an advantage over conventional systems of being able to move onto subsequent sequencing runs while secondary analysis of the reads of a preceding sequencing run is being performed. That is, where conventional nucleic acid sequencers would have needed to wait approx. 24-48 hours after completion of a first sequencing run before commencing a second sequencing run, as shown in FIG. 1A, the nucleic acid sequencer 110 can use the mapping and aligning unit 142a implemented in the programmable circuit 142 to parallelize secondary analysis of reads of the first sequencing run with performance of a second sequencing run. Thus, the nucleic acid sequencer 110 of FIG. 1B can be used to perform more sequencing runs in shorter periods of time than conventional systems that use the system and workflow described by FIG. 1A. Accordingly, parallelizing sequencing runs and secondary analysis by offloading secondary analysis computing tasks to the programmable circuit 142 of the secondary analysis unit 140 can create an increase in revenue from additional reagent sales.

In some implementations, the nucleic acid sequencer 110 can also have software programs such as a demultiplexing unit 162 and a variant calling unit 164 stored in memory 160. One or more processors 150 of the nucleic acid sequencer can process software instructions for these units in order to realize the functionality of these units. For example, in some implementations, DNA fragments of multiple samples may be sequenced at the same time using the nucleic acid sequencer 110. In such instances, the demultiplexing unit 162 can be used to implement demultiplexing techniques that organize the reads based on an index such as a barcode that has been added to each of the generated reads and identify the sample that is associated with each read. By way of another example, the processor 150 can be used to execute the variant calling unit 164 which can analyze mapped and aligned reads to identify the occurrence of any variants such as single nucleotide polymorphisms (SNPs), insertions/deletions (indels), structural variations, or the like. In some implementations, the programmable circuit 142 can be dynamically reconfigured to aid variant calling processing. For example the programmable circuit 142 can be dynamically reconfigured to include an HMM unit that can be used to perform probability calculations as to the likely occurrence of a variant at one or more reference locations of mapped and aligned reads. In some implementations, variant calling unit 164 can be configured to perform variant calling operations of mapped and aligned reads from a Read 1 interval in parallel with sequencing operations of a second sequencing run.

The example of FIG. 1B describes an example having reads with 8 nucleotides. However, the present disclosure is not so limited. Instead, this simple example is presented to explain features of the present disclosure in a manner that is easy to understand. In practice, DNA fragments of the present disclosure may each have, in some implementations, e.g., up to 600 nucleotides, up to 1000 nucleotides, or more, and each read of the fragment may have, e.g., 50 nucleotides, 75 nucleotides, 150 nucleotides, 200 nucleotides, 300 nucleotides, 500 nucleotides, or more, from each end of the DNA fragment. However, implementations of the present disclosure can be employed that have different length DNA fragments and reads of different lengths. Likewise, nothing in FIG. 1B or any other figure should be interpreted as limiting a number of clusters of fragments. For example, a nucleic acid sequencer 110 may perform massively parallel sequencing, with millions of clusters of multiple fragments being sequenced simultaneously.

Figure 2:
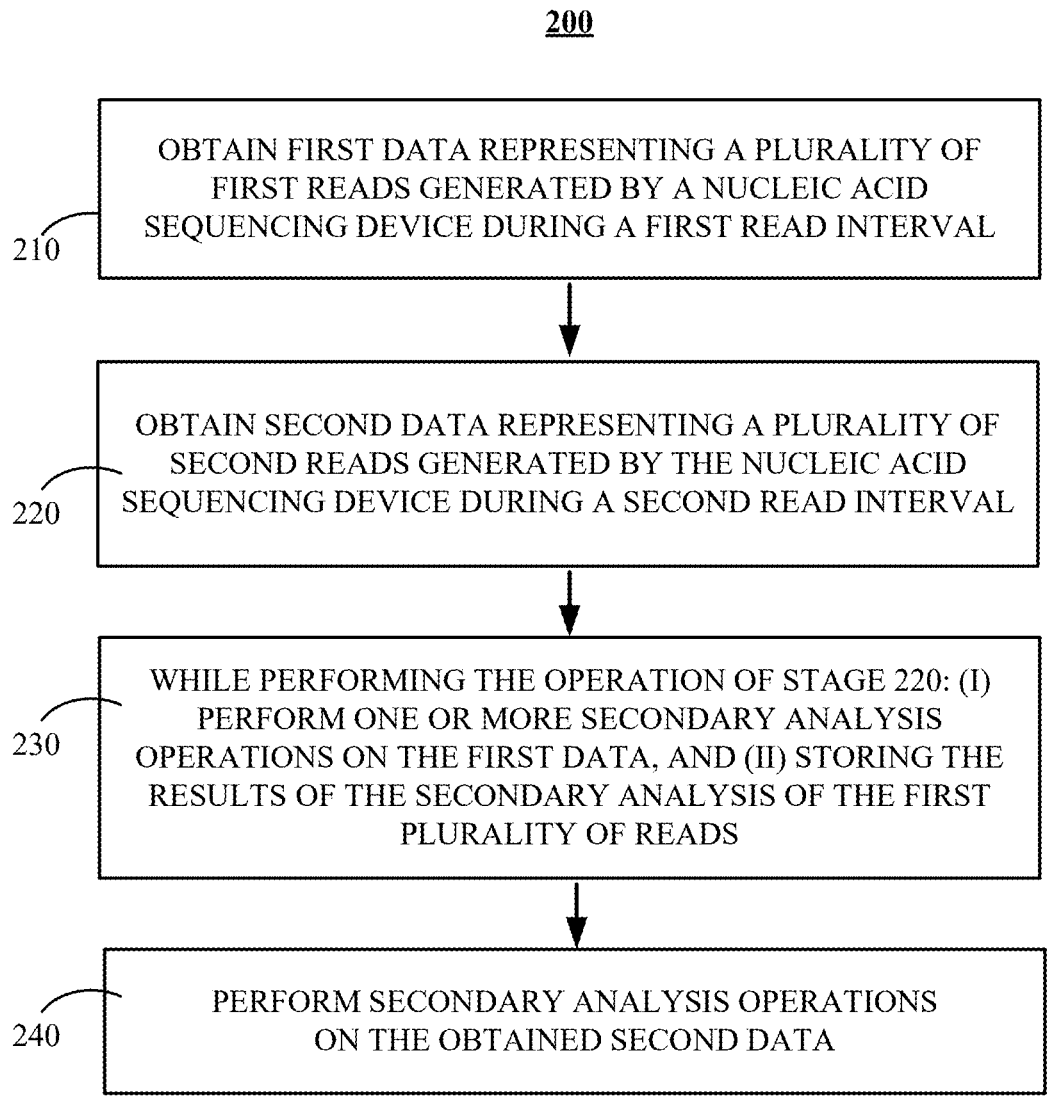
FIG. 2 is a flowchart of an example of a process for performing incremental secondary analysis in accordance with the workflow diagram of FIG. 1B.

FIG. 2 is a flowchart of an example of a process 200 for performing incremental secondary analysis in accordance with the workflow diagram of FIG. 1B. In general, the process 200 includes obtaining first data representing a plurality of first reads generated by a nucleic acid sequencing device during a first read interval (210), obtaining second data representing a plurality of second reads generated by the nucleic acid sequencing device during a second read interval that is performed after the first read interval (220), while the second data is being obtained in stage 220 (I) performing one or more secondary analysis operations on the first data representing the plurality of first reads generated by the nucleic acid sequencer and (II) storing the results of the secondary analysis of the first plurality of reads (230), and, thereafter, performing secondary analysis of the obtained second data representing the second plurality of reads to the reference data. For convenience, these stages will be described in more detail below as being performed by a sequencing system such as system 100 of FIG. 1B.

A sequencing system can begin execution of the process 200 by obtaining 210 first data representing a plurality of first reads generated by a nucleic acid sequencing device during a first read interval. Obtaining the first data can include storing the first data representing the plurality of first reads in a memory device such as a memory device of a secondary analysis unit after the first data is generated by the nucleic acid sequencing device. The memory device of the secondary analysis unit may be a memory unit that is accessible by an integrated circuit of the secondary analysis unit configured to perform secondary analysis operations. The integrated circuit can include one or more programmable circuits, one or more ASICs, or a combination thereof. Each read of the plurality of first reads may be comprised of an ordered sequence of nucleotides. In some implementations, the ordered sequence of nucleotides can correspond to nucleotides of a first end of a nucleic acid fragment. The nucleic acid sequencing device can include any nucleic acid sequencing device including a sequencer capable of sequencing either DNA or RNA.

The sequencing system can continue execution of the process 200 by obtaining 220 second data representing a plurality of second reads generated by the nucleic acid sequencing device during a second read interval that is performed after the first read interval. Obtaining the second data can include storing the second data representing the plurality of second reads in a memory of a secondary analysis unit after the second data is generated by the sequencing device. The memory device of the secondary analysis unit may be a memory unit that is accessible by an integrated circuit of the secondary analysis unit configured to perform secondary analysis operations. The integrated circuit can include one or more programmable circuits, one or more ASICs, or a combination thereof. In some implementation, at least a portion of the second data is obtained while another portion of the second data is being generated by the nucleic acid sequencing device. Each read of the plurality of second reads may be comprised of an ordered sequence of nucleotides. In some implementations, the ordered sequence of nucleotides can correspond to nucleotides of a second end of the nucleic acid fragment that is opposite to the first end of the nucleic acid fragment.

While the sequencing system is obtaining the second data at stage 220, the sequencing system can perform at stage 230 one or more secondary analysis operations on the first data representing the plurality of first reads. In some implementations, performing one or more secondary analysis operations on the first data representing the plurality of first reads can include (i) providing, by the nucleic acid sequencing device, the first data to a mapping and aligning unit to align the first data representing the plurality of first reads to a reference sequence, (ii) aligning, using the mapping and aligning unit, the first data representing the plurality of first reads to a reference sequence, (iii) receiving, from the mapping and aligning unit, alignment results, and (iv) storing the received alignment results of the alignment of the first data representing the plurality of first reads to the reference sequence before completion of the obtaining second data at stage 204. The alignment results can include alignment statistics that describe a quality of the alignment of the first data representing the first plurality of reads to a reference sequence. The alignment statistics can include, for example, one or more of a MAPQ score, an alignment score, or the like. In other implementations, the alignment results can include mapped and aligned reads that can be provided as an input to a variant caller for a determination of potential variants.

In some implementations, output data describing the alignment results can be provided for review by one or more human users. For example, output data describing the alignment results can be output on a display, e.g., coupled to the nucleic acid sequencing device or provided in another room or building. Alternatively, or in addition, output data describing the alignment results can be output using a printer communicatively coupled, e.g., directly or indirectly, to the nucleic acid sequencing device to print a report describing the alignment results.

In some implementations, at least a portion of the mapping and aligning unit is implemented in an integrated circuit such as programmable circuit or ASIC installed in the nucleic acid sequencing device. For example, the programmable circuit or ASIC may implement table look-up functions, a Smith-Waterman algorithm, or quality score determination. However, in other implementations, one or more operations of the mapping and aligning unit may be performed in software executed by the nucleic acid sequencing device. For example, controlling the programmable circuit and the sorting of alignment results may be implemented in software. In yet other implementations, the mapping and aligning unit may be implemented in a programmable circuit, ASIC, executable software, or a combination thereof, in one or more remote computers that is communicatively coupled to the nucleic acid sequencing device using one or more networks. In such implementations, data representing reads, alignment results, and the like can be communicated between the nucleic acid sequencing device and the one or more remote computers hosting the mapping and aligning unit using one or more networks.

The sequencing system, other processing system, or one or more human users can evaluate the alignments results while the second data is being obtained in stage 220. For example, the alignment results can be evaluated to determine whether the alignment is of sufficient quality to continue obtaining second data in stage 220. In some implementations, if the alignment results for the first plurality of reads fail to satisfy a predetermined threshold, then the nucleic acid sequencer can be instructed to stop obtaining the second data in stage 220. Alternatively, if it is determined that the alignment results for the first plurality of reads satisfies the predetermined threshold, then the nucleic acid sequencer can be permitted to continue obtaining the second data in stage 220.

In other implementations, the mapped and aligned first reads can be evaluated for the detection of potential variants between the mapped and aligned first reads and one or more reference sequences while the second data is being obtained at stage 220. Such implementations can enable tertiary analysis of the mapped and aligned first reads to be achieved quicker than conventional methods, which would prohibit the beginning of tertiary analysis until after completion of both the first read interval and the second read interval. Thus, initial diagnosis can be obtained to start treatment as much as 12-24 hours, or more, earlier by not having to wait for the second read interval to complete before proceeding to tertiary analysis.

The sequencing system can continue execution of the process 200 by instructing at stage 240 the performance of secondary analysis operations on the second data, e.g., instructing the mapping and aligning unit to begin alignment of the second data representing the second plurality of reads to the reference sequence. In some implementations, the sequencing system 200 may always proceed to stage 240. Such implementations still provide technical advantages of expediting tertiary analysis and a reduction in the downtime of the nucleic acid sequencing device. However, in other implementations, execution of the process 200 may only continue with instructing the mapping and aligning unit to begin alignment of the second data representing the second plurality of reads to the reference sequence if the received alignment results describing the quality of the alignment of the first data representing the plurality of first reads is determined to satisfy a predetermined quality threshold.

In some implementations, the sequencing system can rely on the secondary analysis results of mapping and aligning, variant calling, or both, of the first data performed at stage 220 while the second data was being obtained. In other implementations, these initial secondary analysis results related to the first data performed at stage 230 can be discarded after they are evaluated to determine quality of the first read interval. In such instances, the sequencing system can initiate a second iteration of the secondary analysis of the first data either before or after secondary analysis of the second data is performed at stage 240.

Figure 3:
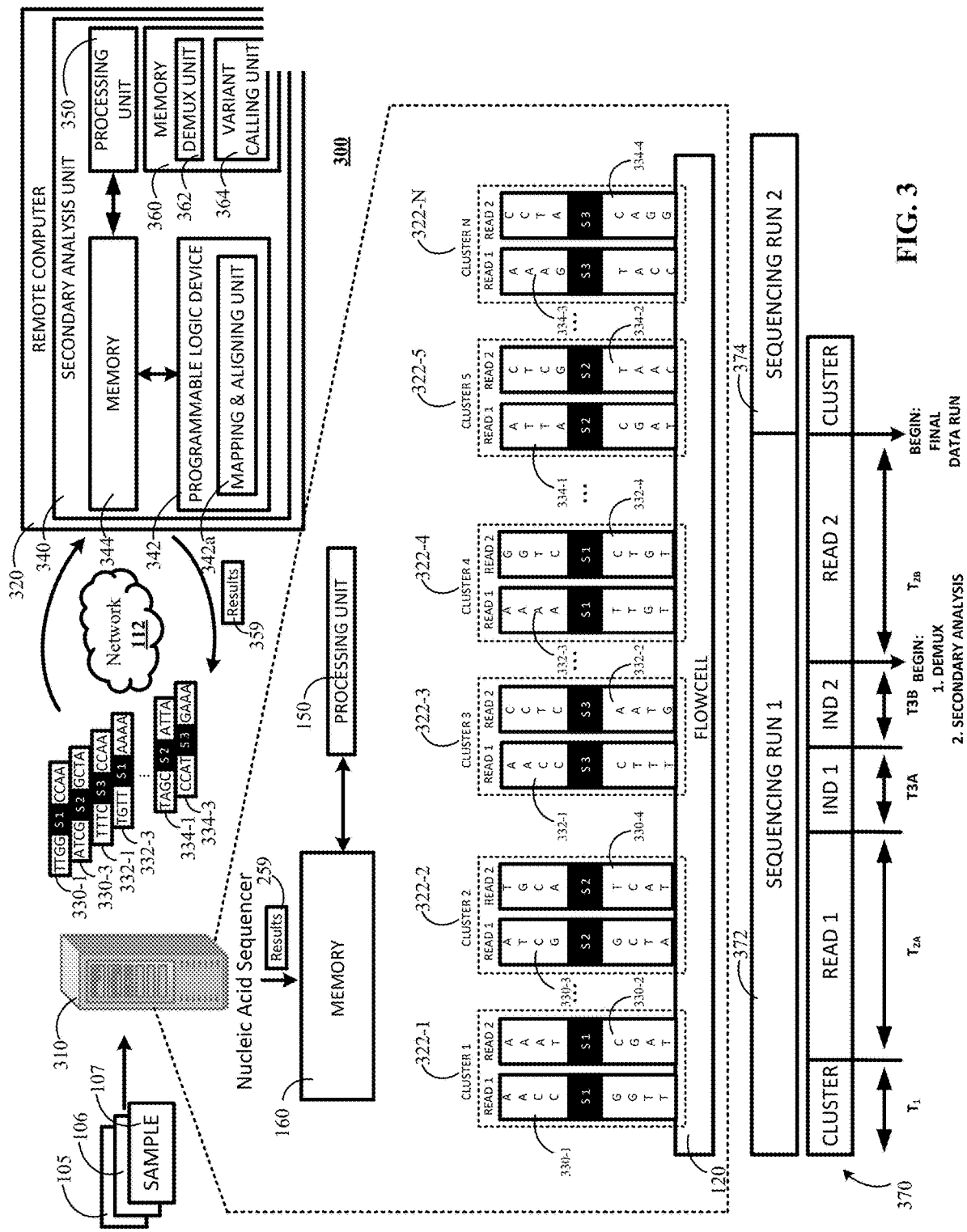
FIG. 3 is a contextual diagram of an example of a system for performing incremental secondary analysis of one or more samples using a secondary analysis unit that is located remote from the nucleic acid sequencer

FIG. 3 is a contextual diagram of an example of a system 300 for performing incremental secondary analysis of one or more samples using a secondary analysis unit 340 that is located remote from the nucleic acid sequencer 310. The system 300 is generally the same as system 100 described with reference to FIG. 1B with a few changes. One change is that the secondary analysis unit 340 is located in one or more computers 320 that are remote from the nucleic acid sequencer 310. For any reference numeral of FIG. 3 not explicitly mentioned, the component identified by the reference numeral has the same features as its corresponding feature in FIG. 1. For example, respective clusters 322-1, 322-2, 322-3, 322-4, 322-5, 322-N have the same meaning as clusters 122-1, 122-2, 122-3, 122-4, 122-5, 122-N, respectively, of FIG. 1, unless additional or different features are described with reference to FIG. 3.

Another difference between the example of FIG. 3 and the example of FIG. 1B is that in the example of FIG. 3, multiple samples are processed. As a result, the reads produced by the nucleic acid sequencer 310 in system 300 have an index that is generated for each read. This index is represented in FIG. 3 by the labels S1, S2, and S3 that are attached to each read. In this example, S2, S2, S3 are strings used to identify reads generated based on a first sample, second sample, or third sample respectively. Though the indexes are described here using a term S1, S2, S3, the present disclosure is not limited to use of text strings as a sample identifier, as these terms are being used as examples to illustrate the concept of an index. Instead, in some implementations, a barcode, or other data, may be used as a sample identifier of a read. In some implementations, the sample identifier can be generated by adding synthetic nucleotides representing the index to each generated read.

With reference to the example of FIG. 3, the nucleic acid sequencer 310 or remote computer 320 can configure the programmable circuit 342 of the secondary analysis unit 340 to include a mapping and alignment unit 342a. The nucleic acid sequencer 310 can receive multiple samples 105, 106, 107. The samples 105, 106, 107 can include, for example, nucleic acid samples from different entities. The different entities can be different persons, different animals, different plants, or the like. The nucleic acid sequencer 310 can prepare the samples 105, 106, 107 and perform cluster generation during time T1 of the workflow 370. The nucleic acid sequencer 310 can perform sequencing operations such as sequencing-by-synthesis of a first read interval to generate first reads 330-1, 330-3, 332-1, 332-3, 334-1, 334-3 during a time T2A that occurs following time T1. At the end of time T1+T2A, the nucleic acid sequencer 310 completes sequencing of the first reads 330-1, 330-3, 332-1, 332-3, 334-1, 334-3 and begins generating indexes for the first reads generated during the first read interval during time T3A. At the end of time T1+T2A+T3A, the nucleic acid sequencer 310 completes index generation for the first read cycle and beings generating indexes for the second reads that will be generated during the second read interval during time T3B. At the end of time T1+T2A+T3A+T3B, the nucleic acid sequencer 310 begins sequencing of the second reads 330-2, 330-4, 332-2, 332-4, 334-2, 334-4.

The nucleic acid sequencer 310 is configured to parallelize secondary analysis operations such as mapping and aligning of the first reads 330-1, 330-3, 332-1, 332-3, 334-1, 334-3 while the nucleic acid sequencer 310 performs sequencing operations such as sequencing-by-synthesis of a second read interval to generate second reads 330-2, 330-4, 332-2, 332-4, 334-2, 334-4 during the time period T2B. This process is similar to that described with reference to the example of FIG. 1B. However, in the example of FIG. 3, multiple samples have been sequenced. Accordingly, the plurality of first reads need to be demultiplexed into groups based on the indexes of each read before proceeding with other secondary analysis operations such as mapping and aligning and variant calling. Once the plurality of first reads are demutliplexed, one or more secondary analysis operations can be performed on the demultiplexed groups of first reads. In some implementations, the system 300 can generate demultiplexing statistics based on the demultiplexing operations and the stored statistics can be evaluated to determine the quality of sequenced reads.

In the example of FIG. 3, secondary analysis of the first reads cannot begin until the end of time T1+T2A+T3A+T3B, because organization of the first reads into demultiplexed groups cannot occur until indexing operations during times T3A and T3B are complete. Once the second index is completed at the end of Time T1+T2A+T3A+T3B, the nucleic acid sequencer 310 can provide the plurality of first reads to the remote computer 320 over the network 112. The remote compute 320 can receive the plurality of first reads and store the plurality of first reads in the memory 344. While the nucleic acid sequencer 310 is performing a second read interval during time T2B, the secondary analysis unit 340 can use the processing unit 350 to access the plurality of first reads in the memory 344 and use the demultiplexing unit 362 to demultiplex the plurality of first reads 330-1, 330-3, 332-1, 332-3, 334-1, 334-3 into groups based on the indexes or sample identifier, of each read. Demultiplexing can be achieved using demultiplexing operations to organize the first reads based on the index. The demultiplexed first reads can be stored in the memory 344. The mapping and aligning unit 342a can then access the reads stored in the memory 344 and perform mapping and aligning operations on the demultiplexed first reads during the second read interval.

The secondary analysis unit 340 can generate statistics that can be used to evaluate the quality of the reads generated by the nucleic acid sequencer. In some implementations, the secondary analysis unit can generate demultiplexing statistics based on the demultiplexing operations. The mapping and aligning unit 342a can generate mapping and aligning results and statistics for each group of first reads stored in the memory 344. The mapping and aligning unit 342a can store results 359 in memory 360 or provide results 359 back to the nucleic acid sequencer 310.

The results 359 can include demultiplexing statistics, mapping and aligning results, mapping and aligning statistics, variant calling statistics, or any combination thereof. The demultiplexing statistics can include a number of reads corresponding to each sample identifier. The mapping and aligning results can include data representing one or more mapped reads to a reference sequence. The mapping and aligning statistics can include data describing, for example, a MAPQ score that provides an indication of mapping quality, an alignment score that provides an indication of alignment quality, or the like. The nucleic acid sequencer 310 can receive the results 359 and store the received results in the memory 160.

In the example of FIG. 3, the ultrafast execution times of the mapping and aligning unit 342a implemented using hardwired logic of the programmable circuit 342 enables the mapping and aligning unit 342a to perform mapping and aligning of the respective demultiplexed groups of first reads 330-1, 330-3, 332-1, 332-3, 334-1, 334-3 in a fraction of the time that is required, by the nucleic acid sequencer 310, to perform the second read interval. For example, in some implementations, the programmable circuit 342a can perform mapping and aligning of the demultiplexed groups of first reads 330-1, 330-3, 332-1, 332-3, 334-1, 334-3 in mere minutes while sequencing of the second reads 330-2, 330-4, 332-2, 332-4, 334-2, 334-4 during the second read interval can take 12 to 24 hours. Accordingly, the results 359 can be evaluated by the nucleic acid sequencer 310, the remote computer 320, a user of the nucleic acid sequencer 310, or remote computer 320, an artificially intelligent agent or model, or a combination thereof, and a determination can be made, based on the quality of the demultiplexing of the first reads 330-1, 330-3, 332-1, 332-3, 334-1, 334-3, the quality of the mapping and alignment of the demultiplexed groups of first reads 330-1, 330-3, 332-1, 332-3, 334-1, 334-3, or both, whether the nucleic acid sequencer 310 should continue sequencing operations during the second read interval to generate the second reads 330-2, 330-4, 332-2, 332-4, 334-2, 334-4.

A determination as to whether sequencing operations during the second read interval to generate the second reads 330-2, 330-4, 332-2, 332-4, 334-2, 334-4 should continue can be made automatically by the nucleic acid sequencer 310, manually by a user of the nucleic acid sequencer, automatically by an artificially intelligent agent or model, or based on data describing a determination from a combination thereof, as described with reference to the example of FIG. 1B. Alternatively, or in addition, the remote computer 320, a user of computer 320, or an artificially intelligent agent or model, or a combination thereof, can determine, based on the results 359, whether or not sequencing during the second read interval to generate the second reads 330-2, 330-4, 332-2, 332-4, 334-2, 334-4 should continue. Such analysis of the results 359 can be evaluated by the remote computer 320, a user of the remote computer 320, an artificially intelligent agent or model, or a combination thereof, in the same manner as described with reference to the evaluation of results 149 by the nucleic acid sequencer 310, user of the nucleic acid sequencer 310, or an artificially intelligent agent or model, or a combination thereof, in the description of FIG. 1B. In the case of an artificially intelligent agent or model, the artificially intelligent model can also be trained on input data types that include demultiplexing characteristics in addition to the other input data types described in the description of FIG. 1B.

In some implementations, the demultiplexing statistics can be evaluated separately from, or in conjunction with, the mapping and aligning statistics to determine a quality of the reads being generated by the nucleic acid sequencer 310. For example, the nucleic acid sequencer 310 or remote computer 320 can store data representing an expected number of reads for each respective sample identifier. The nucleic acid sequencer 310, the remote computer 320, a user, an artificially intelligent agent, or a combination thereof, can then determine whether the demultiplexing statistics include a number of reads corresponding to each sample identifier that is within a threshold amount of error of the expected number of reads for each sample identifier. If the demultiplexing statistics are within the threshold amount of error of the expected number of reads for each sample identifier, the nucleic acid sequencer 310, remote computer 320, a human user, an artificially intelligent agent, or a combination thereof, can determine that the sequencing operations should continue. Alternatively, if it is determined that the demultiplexing statistics are not within a threshold amount of error of the expected number of reads for each sample identifier, then the nucleic acid sequencer 310, remote computer 320, a user, an artificially intelligent agent or model, or a combination thereof, can determine that the sequencing run should be terminated.

In some implementations, it may not be necessary for the results 359 to be transmitted back to the nucleic acid sequencer 310 from the remote computer 320. Instead, the remote computer 320, a user of remote computer 320, or an artificially intelligent agent or model, can transmit data back to the nucleic acid sequencer 310 indicating whether or not the nucleic acid sequencer 310 should continue generation of the second reads 330-2, 330-4, 332-2, 332-4, 334-2, 334-4 based on the computer 320's analysis, a user of computer 320's analysis, or an artificially intelligent agent or model's analysis of the results 359. The nucleic acid sequencer can then determine whether to continue or termination the second read interval based on the data received from the remote computer 320 without actually receiving the results 359.

In yet another implementation, the nucleic acid sequencer can also consider multiple determinations, similar to that described with reference to FIG. 1B. For example, in some implementations, data describing the determination of the nucleic acid sequencer 310, the user of the nucleic acid sequencer 310, the remote computer 320, a user of remote computer 320, an artificially intelligent agent or model, or any combination thereof, can be obtained, and in such implementations, the nucleic acid sequencer 310 will only terminate the second read interval if the nucleic acid sequencer 310, the user of the nucleic acid sequencer 310, the remote computer 320, a user of the remote computer 320, an artificially intelligent agent or model, or any combination thereof, agree that the second read interval should be terminated. In other implementations, an aggregate score can be generated based on weighted average of the determinations of one or more of the nucleic acid sequencer 310, the user of the nucleic acid sequencer 310, the remote computer 320, a user of the remote computer 320, an artificially intelligent agent, or any combination thereof, and then determined, based on the aggregate score, whether the second read interval should be terminated. In such implementations the second read interval may be terminated if the aggregated score falls below a predetermined threshold. Alternatively, the second read interval may be continued if the aggregated score falls above the predetermined threshold.

Using these techniques, the system 300 of FIG. 3 provides similar technological advantages described with reference to FIG. 1B. That is, the system 300 can conserve reagents used to generate second reads if the results 359 indicate that the alignment of the first reads is a low quality alignment. Once a determination has been made that the quality of demultiplexing statistics, mapping and aligning results, mapping and alignment statistics, or combination thereof, is satisfactory, the nucleic acid sequencer 310 can discard the results 359. In other implementations, the mapping and alignment of the first reads performed in parallel with the second read can be used as the mapping and alignment of the first reads for the final data run.

Continuing with the example of FIG. 3, after a determination that the results 359 are satisfactory, the nucleic acid sequencer 310 can continue execution of the second reads. Once the second reads 330-2, 330-4, 332-2, 332-4, 334-2, 334-4 are generated, the nucleic acid sequencer 310 can transmit instructions to the remote computer 320 using the network 112 that instruct the secondary analysis unit 340 to begin its final secondary analysis data run. The final data run can include demultiplexing the second reads 330-2, 330-4, 332-2, 332-4, 334-2, 334-4 into organized groups of second reads based on the sample identifiers of each second read and then mapping and aligning the second reads 330-2, 330-4, 332-2, 332-4, 334-2, 334-4 using the secondary analysis unit 340. In some implementations, if the mapping and aligning results of the organized first set of reads has been discarded, the final data run can perform mapping and aligning operations on both the first reads and the second reads. Because these operations are implemented using the programmable circuit 342a, these operations can be performed in parallel with the second sequencing run 374 and in a fraction of the time required to perform the second sequencing run 374. This provides the advantage over conventional systems of being able to continue subsequent sequencing runs while secondary analysis of the preceding sequencing run 372 is being performed, thereby reducing sequencer downtime that occurs in conventional systems shown in FIG. 1A.

In addition to demultiplexing and mapping and aligning, the secondary analysis unit 340 can also perform variant calling operations. By way of example, the processing unit 350 can be used to execute the variant calling unit 364 which can analyze mapped and aligned reads to identify the occurrence of any variants such as single nucleotide polymorphisms (SNPs), insertions/deletions (indels), structural variations, or the like. In some implementations, the programmable circuit 342 can be dynamically reconfigured, for example by the remote computer 320, to aid variant calling processing. For example the programmable circuit 342 can be dynamically reconfigured to include an HMM unit that can be used to perform probability calculations as to the likely occurrence of a variant at one or more reference locations of mapped and aligned reads. Examples of use of a programmable circuit such an FPGA to perform variant calling operations are described in more detail in, for example, U.S. Pub. No. 2016/0180019, U.S. Pub. No. 2016/0306922, and U.S. Pub. No. 2019-0259468, the entire contents of each of which is hereby incorporated by reference in their entireties.

The example of FIG. 3 describes an example having reads with 8 nucleotides and 3 samples. However, the present disclosure is not so limited. Instead, this simple example is being presented to explain features of the present disclosure in a manner that is easy to understand. In practice, a DNA fragments of the present disclosure may have, in some implementations, e.g., up to 600 nucleotides, up to 800 nucleotides, up to 1,000 nucleotides, or more, and each read of the fragment may have, e.g., 50 nucleotides, 75 nucleotides, 150 nucleotides, 200 nucleotides, 300 nucleotides, 500 nucleotides, or more, from each end of the nucleotide DNA fragment. Likewise, nothing in FIG. 3 or any other figure should be interpreted as limiting a number of clusters of fragments. For example, a nucleic acid sequencer 310 may perform massively parallel sequencing, with millions of clusters of multiple fragments being sequenced simultaneously.

Though the example of FIG. 3 relates to multiple samples that are used to generate reads having an index or sample identifier, the present disclosure is not so limited. Instead, the system 300 can also be used to process a single sample that generates reads that are not indexed—because all the reads belong to the same sample. In such implementations, the same processes could be performed with the second read interval, "Read 2", being initiated immediately after the first read interval "Read 1," without the generation of any indexes. Then, once the first read interval "Read 1" is completed, the second read interval "Read 2" can be initiated while the secondary analysis of the first reads are parallelized with the second read interval. The only substantial difference between the single sample implementation and the multiple sample implementation is that the index generation and demultiplexing stages do not need to be performed in the single sample—as all reads are associated with the same sample.

Figure 4:
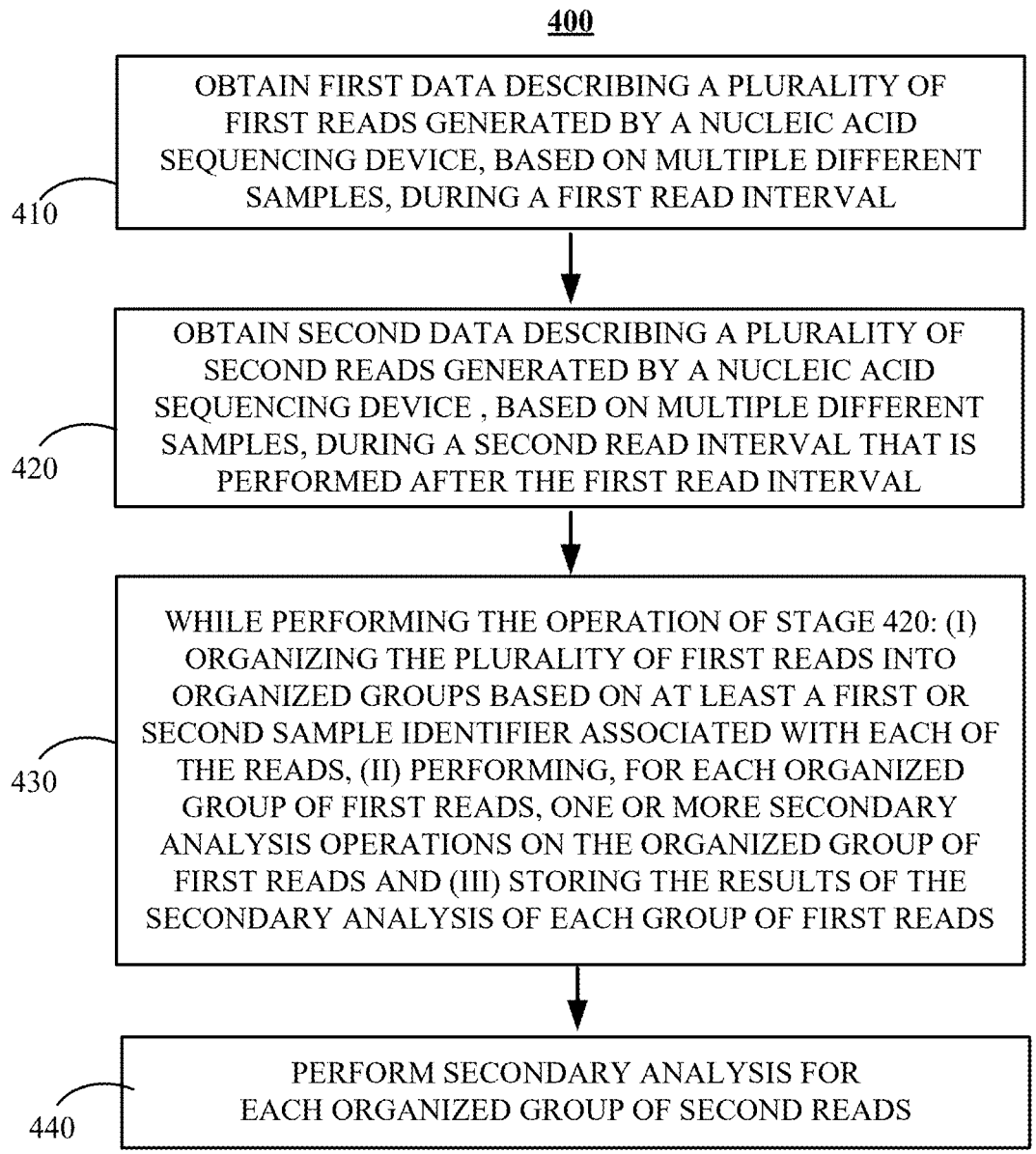
FIG. 4 is a flowchart of an example of a process for performing incremental secondary analysis in accordance with the workflow diagram of FIG. 3.

FIG. 4 is a flowchart of an example of a process 400 for performing incremental secondary analysis in accordance with the workflow diagram of FIG. 3. In general, the process 400 includes obtaining first data describing a plurality of first reads generated by a nucleic acid sequencing device, from multiple different samples, during a first read interval (410), obtaining second data describing a plurality of second reads generated by the nucleic acid sequencing device, from multiple different samples, during a second read interval (420) that is performed after the first read interval (410), while the second data is being obtained in stage 420 (I) organizing the plurality of first reads into organized groups based on a at least a first or second sample identifier associated with each of the first reads, (II) performing, for each organized group of first reads, secondary analysis operations on the organized group of first reads and (III) storing the results of the secondary analysis of each group of first reads (430), and, thereafter, instructing the secondary analysis unit to begin (A) organizing the plurality of second reads into a plurality of organized groups based on at least a first or second sample identifier (440), and (B) performing, for each organized group of second reads, secondary analysis operations on the organized group of second reads, or on the organized group of first and second reads (450). For convenience, and not as a limitation, these stages will be described in more detail below as being performed by a sequencing system such as system 300 of FIG. 3.

A sequencing system can begin execution of the process 400 by obtaining 410 first data describing a plurality of first reads generated by a nucleic acid sequencing device, from multiple different samples, during a first read interval. Obtaining the first data can include storing the first data representing the plurality of first reads in a memory device such as a memory device of a secondary analysis unit after the first data is generated by the sequencing device. The memory device of the secondary analysis unit may be a memory unit that is accessible by an integrated circuit of the secondary analysis unit configured to perform secondary analysis operations. The integrated circuit can include one or more programmable circuits, one or more ASICs, or a combination thereof.

Each read of the plurality of first reads may be comprised of an ordered sequence of nucleotides. In some implementations, the ordered sequence of nucleotides can correspond to nucleotides of a first end of a nucleic acid fragment. The nucleic acid fragment may be have been clonally amplified to facilitate sequencing and, in such implementations, the ordered sequence of nucleotides may be determined by analyzing plurality of clones of the nucleic acid fragment to generated the nucleotides of the read. Each first read can include data identifying the sample used to generate the first read. In some implementations, the data identifying the sample can include a barcode. The nucleic acid sequencing device can include any nucleic acid sequencing device including a DNA sequencer or an RNA sequencer.

The sequencing system can continue execution of the process 400 by obtaining 420 second data describing a plurality of second reads generated by the nucleic acid sequencing device, from multiple different samples, during a second read interval that is performed after the first read interval. Obtaining the second data can include storing the second data representing the plurality of first reads in a memory of the secondary analysis unit after the second data is generated by the sequencing device. The memory device of the secondary analysis unit may be a memory unit that is accessible by an integrated circuit of the secondary analysis unit configured to perform secondary analysis operations. The integrated circuit can include one or more programmable circuits, one or more ASICs, or a combination thereof.

In some implementations, at least a portion of the second data is obtained while another portion of the second data is being generated by the nucleic acid sequencing device. Each read of the plurality of second reads may be comprised of an ordered sequence of nucleotides. In some implementations, the ordered sequence of nucleotides can correspond to nucleotides of a second end of the nucleic acid fragment that is opposite of the first end of the nucleic acid fragment. The nucleic acid fragment may be have been clonally amplified to facilitate sequencing and, in such implementations, the ordered sequence of nucleotides may be determined by analyzing plurality of clones of the nucleic acid fragment to generated the nucleotides of the read. Each second read can include data identifying a sample from which second read originated. In some implementations, the data identifying the sample can include a barcode.

While the second data is being obtained in stage 420 the sequencing system can use a secondary analysis unit to parallelize additional processing of the plurality of first reads. In some implementations, the additional parallelized processing can include (I) organizing the data representing the plurality of first reads into organized groups based on at least a first or second sample identifier associated with each of the first reads, (II) performing, for each organized group of first reads, secondary analysis operations on the organized group of first reads and (III) storing the results of the secondary analysis of each group of first reads (430).

Organizing the plurality of first reads into the organized groups based on the sample identifier is necessary to obtain relevant secondary analysis processing when there are multiple samples being sequenced. This can include performing one or more demultiplexing operations to map the set of first reads having different first sample identifiers to respective organized groups, with each organized group of first reads having the same sample identifier. Demultiplexing statistics can be generated that describe a quality of the demultiplexing operations. For example, the demultiplexing statistics can indicate a number of first reads corresponding to each sample identifier. In some implementations, the secondary analysis unit can return results data to the nucleic acid sequencer, provide the results data to one or more artificially intelligent agents or models, or output the results data to one or more human users that describes the demultiplexing statistics. In such instances, the sequencing system can determine whether to continue with the process 400 or terminate the process 400 at this time, based on the quality of the demultiplex operation described by the demultiplexing statistics. Alternatively, such demultiplexing statistics can be returned as results data after mapping and aligning operations are performed, as described below.

Once the plurality of first reads have been organized, the sequencing system can perform, for each organized group of first reads, one or more secondary analysis operations on the organized group of first reads. Performing secondary analysis operations on the organized group of first reads can include, for each organized group of first reads, (I) providing, by the nucleic acid sequencing device, the organized group of first reads to a mapping and aligning unit to align the organized group of first reads to a reference sequence, (II) aligning, using the mapping and aligning unit, the organized group of first reads to a reference sequence, (iii) receiving, from the mapping and aligning unit, a result, and (iv) storing the received result data before completion of the obtaining of the second data at stage 420.

The results data can include demultiplexing statistics or mapping and aligning statistics. The demultiplexing statistics can include data describing the quality of the demultiplexing operation such as a number of first reads corresponding to each sample identifier. The mapping and aligning statistics can include data describing a quality of the alignment of each organized group of first reads to a respective reference sequence. The mapping and alignment statistics can include, for example, one or more of a MAPQ score, an alignment score, or the like. In other implementations, the mapping and alignment results can include mapped and aligned reads for each organized group of first reads that can be provided as an input to a variant caller for a determination of potential variants between the mapped and aligned reads for each organized group of first reads and a respective reference sequence.

In some implementations, output data describing the results data for each organized group of first reads can be provided for review by one or more human users. For example, output data describing the results data for each organized group of first reads can be output on a display coupled, e.g., to the nucleic acid sequencing device or provided in another room or building. Alternatively, or in addition, output data describing the results data for each organized group of first reads can be output using a printer communicatively coupled, e.g., directly or indirectly, to the nucleic acid sequencing device to print a report describing the alignment results for each organized group of first reads.

In some implementations, the sequencing system, a remote computer, one or more human users, an artificially intelligent agent or model, or a combination thereof, can evaluate the results data while the second data is being obtained in stage 420. For example, the results data can be evaluated to determine whether the demultiplexed first reads, mapping and alignment of the first reads, or both, is of sufficient quality to continue obtaining second data in stage 420. In some implementations, if the results data for the organized groups of first reads does not satisfy one or more predetermined rules or thresholds, then the nucleic acid sequencer can be instructed to stop obtaining the second data in stage 420. Alternatively, if it is determined that the results data for the organized groups of first reads satisfies the one or more predetermined rules or thresholds, then the nucleic acid sequencer can be permitted to continue obtaining the second data in stage 420.

In some implementations, each organized group of mapped and aligned first reads can be evaluated for the detection of potential variants while the second data is being obtained at stage 420. Such implementations can enable tertiary analysis of the variants identified for each group to be achieved quicker than conventional methods, which would prohibit the beginning of tertiary analysis until after completion of both the first read interval and the second read interval. Thus, initial diagnosis can be obtained to start treatment as much as 12-24 hours earlier than conventional methods by not having to wait for the second read interval to complete before proceeding to tertiary analysis.

The sequencing system can continue execution of the process 400 by instructing, at stage 430, the mapping and aligning unit to begin organizing the plurality of second reads into a plurality of organized groups of second reads based on at least a first or a second sample identifier. Organizing the plurality of second reads into the organized groups based on the second sample identifiers is necessary to obtain relevant secondary analysis processing of the second reads. This can include performing one or more demultiplexing operations to map the set of second reads having different sample identifiers to different organized groups, with each organized group of second reads having the same second sample identifier. The sequencing system can continue execution of the process 400 performing, for each organized group of second reads, secondary analysis operations on the organized group of second reads (stage 440). In some implementations the secondary analysis operations can be performed on a combination of the first and the second reads.

In some implementations, the sequencing system may proceed to stages 430 and 440. Such implementations still provide technical advantages of expediting tertiary analysis and reduction in downtime for the nucleic acid sequencer. However, in other implementations, execution of the process 400 by the sequencing system may only continue with organizing the plurality of second reads into a plurality of organized groups (430) and perform secondary analysis operations such as mapping and aligning, variant calling, or both, if the received results data for each of the organized groups of first reads describing the demultiplex quality of the first reads, the mapping and alignment quality of the first reads, or both, is determined to satisfy one or more predetermined quality rules or thresholds.

In some implementations, the sequencing system can rely on the secondary analysis results of mapping and aligning, variant calling, or both, of the organized groups of first reads performed at stage 420 while the second data was being obtained. In other implementations, these initial secondary analysis results related to the organized groups of first reads performed at stage 420 can be discarded after they are evaluated to determine quality of the first read interval. In such instances, the sequencing system can initiate second iteration of the secondary analysis of the organized groups of first reads either before or after secondary analysis of the organized groups of second reads at stages 430 and 440 is completed.

Figure 5:
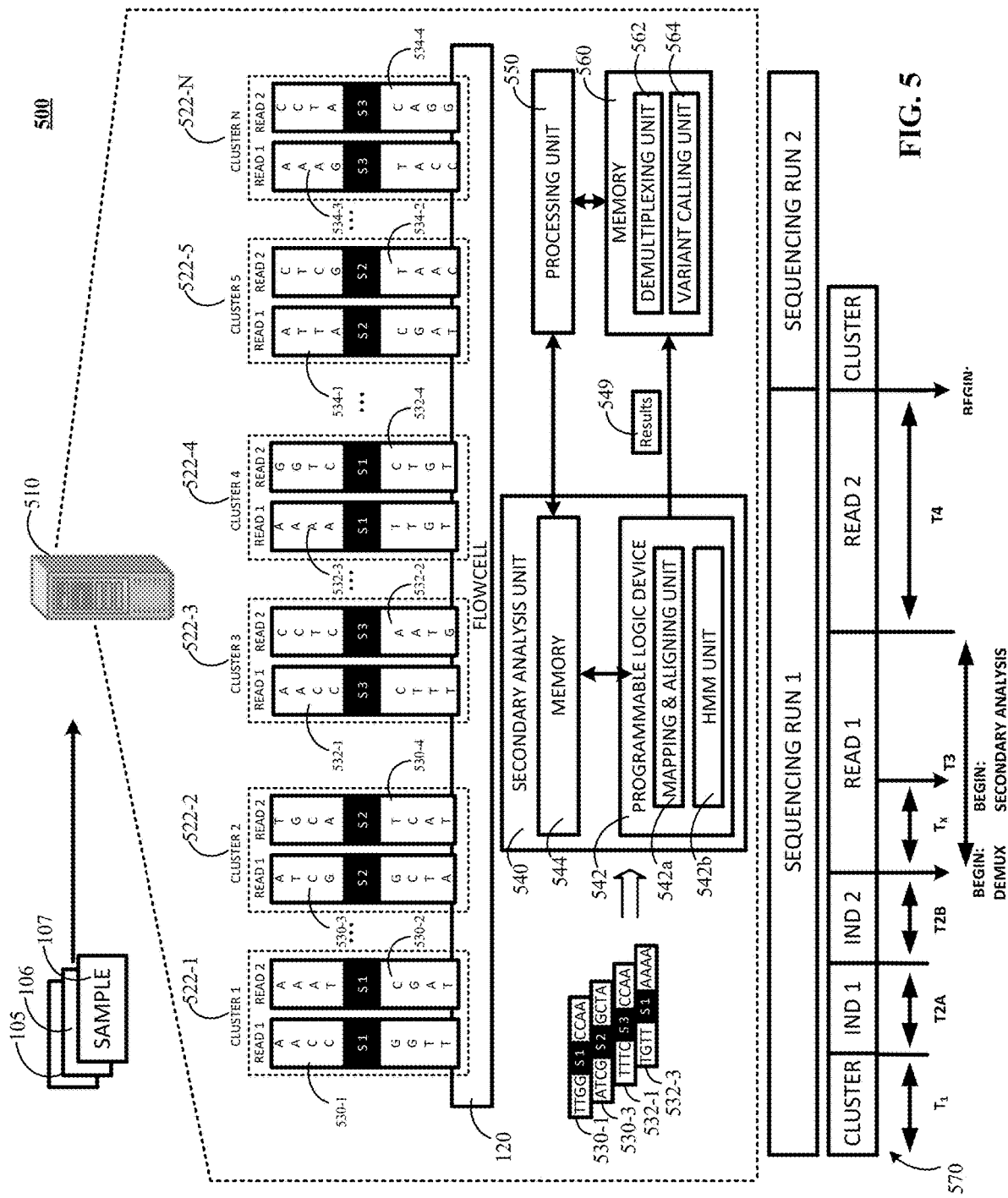
FIG. 5 is a contextual diagram of an example of a system for performing incremental secondary analysis of one or more samples using a secondary analysis unit within a nucleic acid sequencer.

FIG. 5 is a contextual diagram of an example of a system 500 for performing incremental secondary analysis of one or more samples using a secondary analysis unit within a nucleic acid sequencer. The system 500 is generally the same as system 300 described with reference to FIG. 3 with a few differences. One difference is that the secondary analysis unit 540 is located within the nucleic acid sequencer 510. For any reference numeral of FIG. 5 not explicitly mentioned, the component identified by the reference numeral has the same features as its corresponding feature in FIG. 1 or 3. By way of example, respective clusters 522-1, 522-2, 522-3, 522-4, 522-5, 522-N have the same meaning as clusters 122-1, 122-2, 122-3, 122-4, 122-5, 122-N, respectively, of FIG. 1, unless additional or different features are described with reference to FIG. 5.

Figure 6:
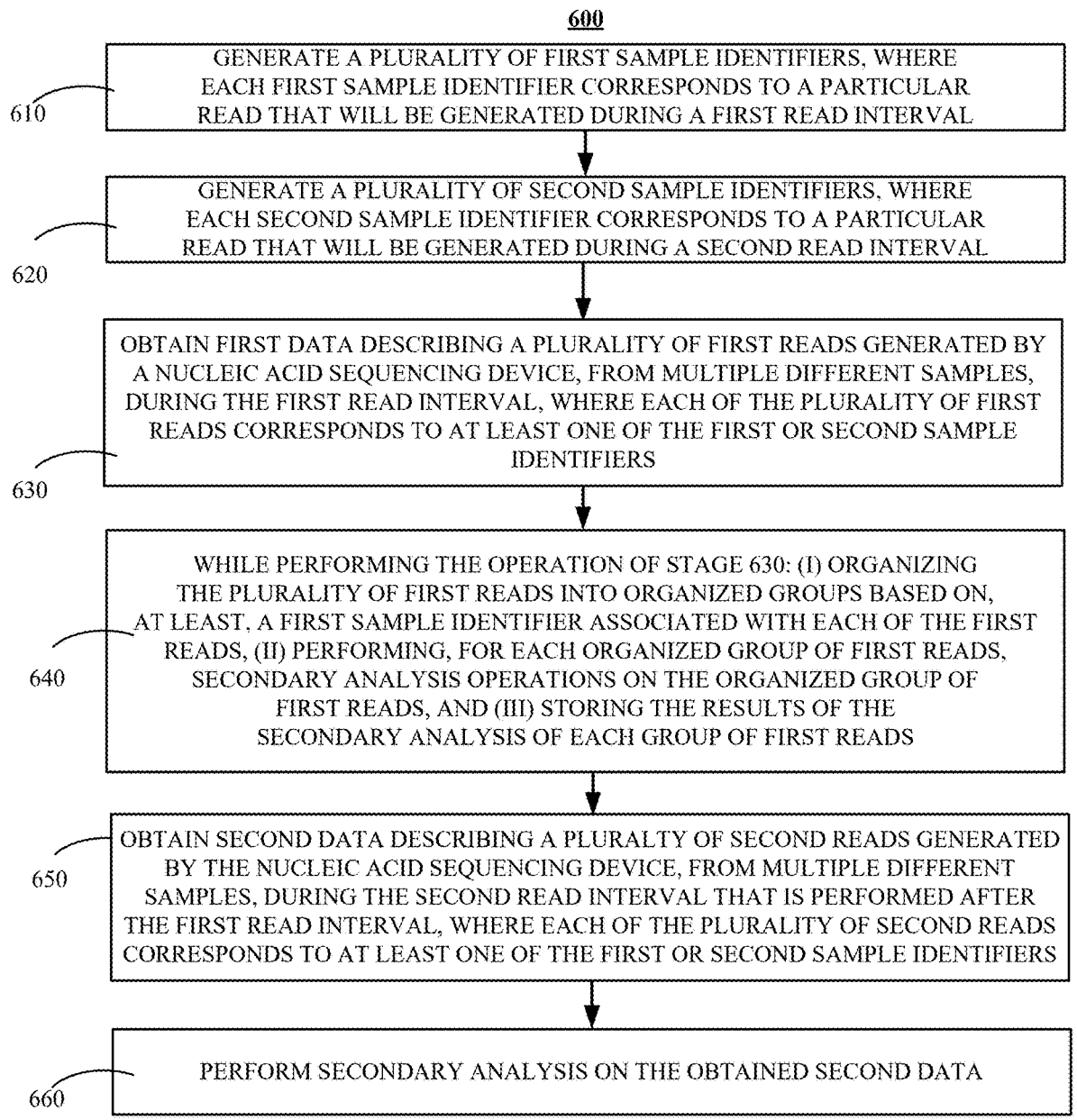
FIG. 6 is a flowchart of an example of a process for performing incremental secondary analysis in accordance with the workflow diagram of FIG. 5.

Another difference between the example of FIG. 5 and the example of FIG. 3 is that the nucleic acid sequencer has been configured to generate sample identifiers or indexes for each read prior to the first read interval. This is illustrated in the workflow 570, which shows that IND1 and IND2 are generated following the clustering stage and prior to the first read the first read interval "READ 1" of workflow 570. This is different than the generation of the sample identifiers or indexes in the example of FIG. 3, as the indexes of FIG. 3 are generated after the first read interval. Though the implementation of FIGS. 5 and 6 are described as generated separate sample identifiers or indexes for "READ 1" and "READ 2," the present disclosure is not so limited. Instead, implementations of the present disclosure may only generate a single sample identifier or index identifier that refers to both "READ 1" and "READ 2" of a particular fragment.

The benefit of generating the sample identifier prior to the first read intervals that organizing reads into demultiplexed groups having the same sample identifier can be performed at runtime, as reads are generated. Given the generation of all sample identifiers and the ability to organize reads based on sample identifiers at runtime, the system 500 is able to begin secondary analysis of organized groups of first reads during the first read interval. In such a scenario, secondary analysis results data including demultiplexing statistics, mapping and aligning statistics, or both, for each organized group of first reads, can be obtained and evaluated during a first read interval-thus enabling the option to terminate the first read interval if the results data is indicating less than satisfactory results, thereby conserving reagent.

Moreover, the ability to begin performing secondary analysis of organized groups of first reads during a first read interval enables an even faster transition to tertiary analysis operations than the examples of systems described with reference to FIG. 1B and FIG. 3. The system of FIG. 5 can transition to tertiary analysis faster than the systems of FIG. 1B and FIG. 3 because an initial set of variants, based on mapped and aligned first reads and used as inputs for tertiary analysis, can be identified during the first read interval. This enables the start of tertiary analysis within less than in about hours from beginning of the first read interval. That is in contrast to the examples of FIG. 1B and FIG. 3, which could not start tertiary analysis using identified variants of mapped and aligned reads as inputs until after the sequencing is complete, respectively.

With reference to the example of FIG. 5, the nucleic acid sequencer 510 can configure the programmable circuit 542 of the secondary analysis unit 540 to include a mapping and alignment unit 542a. The nucleic acid sequencer 510 can receive multiple samples 105, 106, 107. The samples 105, 106, 107 can include, for example, nucleic acid samples from different species. The different species can be different persons, different animals, different plants, or the like. The nucleic acid sequencer 510 can prepare the samples 105, 106, 107 and perform cluster generation during time T1 of the workflow 570.

At the conclusion of the cluster stage, the nucleic acid sequencer 510 begins generating indexes, or sample identifiers, for each first read that will be produced by the nucleic acid sequencer 510 during time T2A. At the end of time T2A, the nucleic acid sequencer 510 begins generated indexes or sample identifiers for each second read that will be produced by the nucleic acid sequencer 510 during time T2B. The index, or sample identifier for each read can include any data that can be used to create a logical relationship between a read and a sample. Thus, at the end of Time T1+T2A+T2B in the example of FIG. 5, indexes, or sample identifiers, index have been created for each first read that will be generated by the nucleic acid sequencer 510 during the first read interval, and indexes, or sample identifiers have also been created for each second read that will be generated by the nucleic acid sequencer 510 during the second read interval.

The nucleic acid sequencer 510 is configured to parallelize secondary analysis operations such as mapping and aligning of at least a portion of the first reads 530-1, 530-3, 532-1, 532-3, 534-1, 534-3 while the nucleic acid sequencer 510 continues to perform sequencing operations such as sequencing-by-synthesis of a first read interval during time T3. Beginning secondary analysis of at least a portion of the first reads during the first read interval could not be achieved in the example of FIG. 3 because the indexes, or sample identifiers for each read were not generated until after the first read interval was complete. In contrast, in the example of FIG. 5, the indexes, or sample identifiers index for each read that is to be generated by the nucleic acid sequencer 510, are created in advance.

In the example of FIG. 5, the first read interval does not begin until after the time T1+T2A+T2B of workflow 570 is complete. After the expiration of T1+T2A+T2B, the nucleic acid sequencer 570 can begin the first read interval. Beginning the first read interval can include initiating primary analysis sequencing operations such as sequencing-by-synthesis to generate one or more first reads 530-1, 530-3, 532-1, 532-3, 534-1, 534-3. After time TX from the beginning of the first read interval "Read 1," one or more first reads 530-1, 530-3, 532-1 that have been generated during time TX can then be stored in the memory 544 of the secondary analysis unit 540 or other memory that is accessible by the secondary analysis unit 540, the processing unit 150, or both.

Because the nucleic acid sequencer 510 is sequencing multiple samples, the nucleic acid sequencer 510 needs to perform an organization operation to organize the one or more first reads 530-1, 530-3, 532-1 into one or more organized groups of first reads. Organizing the first reads can be achieved using the demultiplexing unit 562. For example, the processing unit 550 can access the one or more reads stored in the memory 544, memory 560, or other memory, and execute the programmed functionality of the demultiplexing unit 562 to demultiplex the one or more first reads 530-1, 530-3, 532-1 into one or more organized groups of first reads. Demultiplexing can be achieved using one or more demultiplexing operations to organize the one or more first reads 530-1, 530-3, 532-1 based on the index or sample identifier for the respective first reads. The demultiplexed first reads can be stored in the memory 544 or other memory accessible to the mapping and aligning unit 542a.

The mapping and aligning unit 542a can access the organized first reads stored in the memory 544 and perform real-time mapping and aligning operations on the demultiplexed first reads during the first read interval. The secondary analysis unit 540 can generate results 549 for each group of first reads stored in the memory 544. The results 549 can include demultiplexing statistics, mapping and aligning statistics, mapping and aligning results, or a combination thereof. The secondary analysis unit 540 can store the received results in the memory 560. The demultiplexing statistics can include data describing a demultiplex quality such as a number of records corresponding to each sample identifier. The mapping and aligning statistics such as, for example, a MAPQ score that provides an indication of mapping quality of each group of first reads, an alignment score that provides an indication of alignment quality of each group of first reads, or the like. The mapping and aligning results 549 can include data describing the mapped and aligned reads. In some implementations, these mapping and aligning results can be dynamically updated as more first reads are generated and mapped and aligned to respective reference sequences.

In the example of FIG. 5, the ultrafast execution times of the mapping and aligning unit 542a implemented using hardwired logic of the programmable circuit 542 enables the mapping and aligning unit 542a to perform mapping and aligning of the respective demultiplexed groups of first reads 530-1, 530-3, 532-1, 532-3, 534-1, 534-3 in a fraction of the time that is required, by the nucleic acid sequencer 510, to perform the first read interval. For example, in some implementations, the programmable circuit 542a can perform mapping and aligning of the demultiplexed groups of first reads generated during time TX in hardwired logic during the first read interval "Read 1" in minutes, or less, while execution of the entire first read interval using software executed by the processing unit 150 can take 12 to 24 hours. Thus, the nucleic acid sequencer 510 or one or more human users can evaluate the results 549 of secondary analysis of the first reads such as those first reads generated during time TX while the remainder of the first reads are generated by the nucleic acid sequencer 510 during time T3. Then, the nucleic acid sequencer 510, a user of the nucleic acid sequencer 510, an artificially intelligent agent or model, or a combination thereof, can make a determination, based on the quality of the demultiplexing operation, the mapping and aligning operation, or both, by the results 549 whether the nucleic acid sequencer 510 should continue performance of sequencing operations during the first read interval. This determination as to whether sequencing operations during the first read interval should be continued can be made automatically by the nucleic acid sequencer 510, automatically by an artificially intelligent agent or model, a user of the nucleic acid sequencer, or based on data describing a determination from each of these entities as described with reference to the example of FIG. 1B.

Using these techniques, the system 500 of FIG. 5 provides even better technological advantages described with reference to FIG. 1B. That is, the system 500 can conserve reagents that would be used to continue generating additional reads during the first read interval if the results 549 indicates that the demultiplexing of at least a portion of the first reads already generated during the first read interval, alignment of a portion of the first reads already generated during the first read interval, or both, is of low quality. Once a determination has been made that the demultiplex quality of the already generated first reads, mapping and alignment quality of the already generated first reads, or both, is satisfactory, the nucleic acid sequencer 510 can discard the mapping and aligning results 549. In other implementations, the mapping and alignment of the already generated first reads performed in parallel with the first read interval can be used as the mapping and alignment of the final data run of the first reads.

In addition to demultiplexing and mapping and aligning, the secondary analysis unit 540 can also perform variant calling operations of the one or more groups of mapped and aligned first reads during the first read interval "Read 1." By way of example, the processing unit 550 can be used to execute the variant calling unit 564 which can analyze mapped and aligned reads to identify the occurrence of any variants such as single nucleotide polymorphisms (SNPs), insertions/deletions (indels), structural variations, or the like. In some implementations, the programmable circuit 542 can be dynamically reconfigured, for example by the nucleic acid sequencer 510, to aid variant calling processing. For example the programmable circuit 542 can be dynamically reconfigured to include an HMM unit that can be used to perform probability calculations as to the likely occurrence of a variant at one or more reference locations of mapped and aligned reads. The nucleic acid sequencer 510, or other computer device, can then perform one or more tertiary analysis operations, during the first read interval "Read 1," using any identified variants. This can help expedite treatment to an entity based on the tertiary analysis. An entity can include a patient, person, subject, plant, animal, or the like.

In the example of system 500, if a determination is made to terminate the first read interval based on a determination that the demultiplexing statistics, mapping and aligning statistics, or both, are of low quality, the system 500 may also terminate the second read interval "Read 2." Thus, the system 500 provides additional advantages over the examples of the system of FIG. 1B or FIG. 3 in that even more reagent can be conserved in the event low quality demultiplexing results, mapping and aligning results, or both, are detected.

However, with reference to the example of system 500, if a determination is made that the demultiplexing results, mapping and aligning results, or both, satisfy a threshold level of quality, then the system 500 can begin execution of the second read interval "Read 2," as shown in workflow 570. In some implementations, the system 500 can generate the second read interval "Read 2" without parallelizing the secondary analysis of the second reads. Such execution may be preferable because, for example, the system 500 would already have evaluated the sequencing quality during the first read interval "Read 1." However, in other implementations, the system 500 can parallelize the secondary analysis of the second reads in the same manner as secondary analysis of the first reads was parallelized with the first read interval.

The example of FIG. 5 describes an example having reads with 8 nucleotides and 3 samples. However, the present disclosure is not so limited. Instead, this simple example is being presented to explain features of the present disclosure in a manner that is easy to understand. In practice, a DNA fragments of the present disclosure may have, in some implementations, e.g., up to 600 nucleotides, up to 800 nucleotides, up to 1,000 nucleotides, or more, and each read of the fragment may have, e.g., 50 nucleotides, 75 nucleotides, 150 nucleotides, 200 nucleotides, 300 nucleotides, 500 nucleotides, or more, from each end of the DNA fragment. Likewise, nothing in FIG. 5 or any other figure should be interpreted as limiting a number of clusters of fragments. For example, a nucleic acid sequencer 510 may perform massively parallel sequencing, with millions of clusters of multiple fragments being sequenced simultaneously.

Though the example of FIG. 5 relates to multiple samples that are used to generate reads having an index or sample identifier, the present disclosure is not so limited. Instead, the system 500 can also be used to process a single sample that generates reads that are not indexed—because all the reads belong to the same sample. In such implementations, the same processes could be performed with the first read interval being initiated immediately after the clustering stage. Then, once a portion of the first reads are generated during the first read interval "Read 1," the system 500 can provide the generated portion of the first reads to the mapping and aligning unit 542*a* for mapping and aligning while the remaining portion of the first reads are generated during the first read interval without the need to perform the demultiplexing stage. In this implementation, the first reads do not need to be demultiplexed because they are all associated with the same sample. Similarity, the portion of the mapped and aligned first reads can then be analyzed for variants using the first read interval "Read 1," as described above. Similar determinations can be made as to whether to continue with the first read interval and second read interval as explained with respect to the example FIG. 5. In sum, the substantive difference between a single sample implementation of system 500 of FIG. 5 and the multiple sample implementations of FIG. 5 is that with the single sample implementation, the demultiplexing stages do not need to be performed.

FIG. 6 is a flowchart of an example of a process 600 for performing incremental secondary analysis in accordance with the workflow diagram of FIG. 5. In general, the process 600 includes generating a plurality of first sample identifiers, where each first sample identifier corresponds to a particular read that will be generated during a first read interval (610), generating a plurality of second sample identifier, where each second sample corresponds to a particular read that will be generated during a second read interval (620), obtaining first data describing a plurality of first reads generated by a nucleic acid sequencing device, from multiple different samples, during the first read interval, where each of the plurality of first reads corresponds to at least one of the first or second sample identifiers (630), while obtaining the first data at stage 630 (I) organizing the plurality of first reads into organized groups based on at least a first or second sample identifier associated with each of the first reads, (II) performing, for each organized group of first reads, secondary analysis operations on the organized group of first reads and (III) storing the results of the secondary analysis of each group of first reads (640), obtaining second data describing a plurality of second reads generated by the nucleic acid sequencing device, from multiple different samples, during the second read interval that is performed after the first read interval, where each of the plurality of second reads corresponds to at least one of the first or second sample identifiers (650), and performing secondary analysis on the obtained second data (660). For convenience, and without limitation, these stages will be described in more detail below as being performed by a sequencing system such as system 500 of FIG. 5.

A sequencing system can begin execution of the process 600 by generating 610 a plurality of first sample identifiers, where each first sample identifier corresponds to a particular read that will be generated during a first read interval. In some implementations, each first sample identifier can include an index tag sequence. The index tag sequence may be attached to a target polynucleotides of each sample before the respective samples are immobilized for sequencing. The index tag may be a synthetic sequence of nucleotides which is added to the target as part of the template preparation step. Accordingly, a library-specific index tag is a nucleic acid sequence tag which is attached to each of the target molecules of a sample, the presence of which is indicative of or is used to identify the entity from which the target molecules were isolated. In some implementations, the index tag sequence can include a barcode embedded into the synthetic sequence.

The sequencing system can continue execution of the process 600, at stage 620, by generating a plurality of second sample identifiers, where each second sample identifier corresponds to a particular read that will be generated during a second read interval that occurs after the first read interval. In some implementations, each second sample identifier can include an index tag sequence. The index tag sequence may be attached to a target polynucleotides of each sample before the respective samples are immobilized for sequencing. The index tag may be a synthetic sequence of nucleotides which is added to the target as part of the template preparation step. Accordingly, a library-specific index tag is a nucleic acid sequence tag which is attached to each of the target molecules of a sample, the presence of which is indicative of or is used to identify the entity from which the target molecules were isolated. In some implementations, the index tag sequence can include a barcode embedded into the synthetic sequence.

The sequencing system can continue execution of the process 600, at stage 630, by obtaining first data describing a plurality of first reads generated by a nucleic acid sequencing device, from multiple different samples, during the first read interval, where each of the plurality of first reads corresponds to one of the first sample identifiers. Obtaining the first data can include storing the first data representing one or more first reads in a memory of a secondary analysis unit after the first data is generated by the sequencing device. The memory device of the secondary analysis unit may be a memory unit that is accessible by an integrated circuit of the secondary analysis unit configured to perform secondary analysis operations. The integrated circuit can include one or more programmable circuits, one or more ASICs, or a combination thereof. In one implementation, at least a portion of the first data is obtained while another portion of the first data is being generated by the nucleic acid sequencing device. That is, data representing a first set of one or more reads can be obtained and stored in a memory of the secondary analysis unit while one or more other first reads are generated by the nucleic acid sequencing device during the first read interval.

Each read of the plurality of first reads may be comprised of an ordered sequence of nucleotides. In some implementations, the ordered sequence of nucleotides can correspond to nucleotides of a first end of the nucleic acid fragment. The nucleic acid fragment may be have been clonally amplified to facilitate sequencing and, in such implementations, the ordered sequence of nucleotides may be determined by analyzing plurality of clones of the nucleic acid fragment to generated the nucleotides of the read. Each first sample identifier of each first read, generated in advance of the first read interval, corresponds respectively to a particular sample from which the first read originated. The first sample identifier can be used by the sequencing system to determine a sample associated with any particular first read. In some implementations, the data identifying the sample can include a barcode.

While obtaining the first data at stage 630 during the first read interval, the sequencing system can use a secondary analysis unit to parallelize additional processing of one or more of the first reads, in real time, that have already been generated by the nucleic acid sequencer. In some implementations, the additional processing can include (I) organizing the plurality of first reads into organized groups based on at least a first or a second sample identifier associated with each of the first reads, (II) performing, for each organized group of first reads, secondary analysis operations on the organized group of first reads and (III) storing the results of the secondary analysis of each group of first reads (stage 640).

Organizing the one or more first reads into the organized groups based on the sample identifier is necessary to obtain relevant secondary analysis processing when multiple samples are sequenced. This can include performing one or more demultiplexing operations to map the one or more first reads having different first sample identifiers to respective organized groups, with each organized group of first reads having the same sample identifier. Demultiplexing statistics can be generated that describe the quality of the demultiplex operations. For example, the demultiplexing statistics can indicate a number of first reads corresponding to each sample identifier. In some implementations, the secondary analysis unit can return results data to the nucleic acid sequencer, provide the results data to one or more artificially intelligent agents or models, or output the results data to one or more human users that describes the demultiplexing statistics. In such instances, the sequencing system can determine whether to continue with the process 600 or terminate the process 600 at this time, based on the quality of the demultiplex operation described by the demultiplexing statistics. Alternatively, such demultiplexing statistics can be returned as results data after mapping and aligning operations are performed, as described below.

Once the one or more first reads have been organized, the sequencing system can perform, for each organized group of first reads, one or more secondary analysis operations on the organized group of first reads in parallel with the remainder of first read interval using a secondary analysis unit. Performing secondary analysis operations on the organized group of first reads can include, for each organized group of first reads, (I) providing, by the nucleic acid sequencing device, the organized group of first reads to a mapping and aligning unit to align the organized group of first reads to a reference sequence, (II) aligning, using the mapping and aligning unit, the organized group of first reads to a reference sequence, (III) receiving, from the mapping and aligning unit, results data, and (IV) storing the received alignment results data before completion of the obtaining of the first data at stage 630.

The results data can include demultiplexing statistics or mapping and aligning statistics. The demultiplexing statistics can include data describing the quality of the demultiplexing operation such as a number of first reads corresponding to each sample identifier. The mapping and aligning statistics can include data describing a quality of the alignment of each organized group of first reads to a respective reference sequence. The mapping and aligning statistics can include, for example, one or more of a MAPQ score, an alignment score, or the like. In other implementations, the mapping and aligning results can include mapped and aligned reads for each organized group of first reads that can be provided as an input to a variant caller for a determination of potential variants between the mapped and aligned reads for each organized group of first reads and a respective reference sequence.

In some implementations, output data describing the results data for each organized group of first reads can be provided for review by one or more human users. For example, output data describing the results data for each organized group of first reads can be output on a display, e.g., coupled to the nucleic acid sequencing device or provided in another room or building. Alternatively, or in addition, output data describing the alignment results for each organized group of first reads can be output using a printer communicatively coupled, e.g., directly or indirectly, to the nucleic acid sequencing device to print a report describing the alignment results for each organized group of first reads.

In some implementations, the sequencing system, one or more human users, one or more artificially intelligent agents or models, or a combination thereof, can evaluate the alignments results while the first data is being obtained in stage 630. For example, the results data can be evaluated to determine whether the demultiplexing of the obtained first reads, the mapping and alignment of the obtained first reads, or a combination of both, is of sufficient quality to continue obtaining first data in stage 630. In some implementations, if the results data for the organized groups of first reads does not satisfy one or more predetermined rules or thresholds, then the nucleic acid sequencer can be instructed to stop obtaining the first data during the first read interval in stage 630. Alternatively, if it is determined that the results data for the organized groups of first reads satisfies the one or more predetermined rules or thresholds, then the nucleic acid sequencer can be permitted to continue obtaining the first data during the first read interval in stage 630.

In some implementations, each organized group of mapped and aligned first reads can be evaluated for the detection of potential variants while the first data is being obtained at stage 630. Such implementations can enable tertiary analysis of the variants identified for each group to be achieved quicker than conventional methods, which would prohibit the beginning of tertiary analysis until after completion of both the first read interval in stage 630 and the second read interval in stage 650. Thus, initial diagnosis can be obtained in order to start treatment days earlier than conventional methods, shown in FIG. 1A, by not having to wait for completion of the first read interval, second read interval, and mapping and aligning of the first and second reads before proceeding to tertiary analysis.

At the conclusion of stage 630, the sequencing system can continue execution of the process 600 by obtaining 650 second data describing a plurality of second reads generated by the nucleic acid sequencing device, from multiple different samples, during the second read interval that is performed after the first read interval, where each of the plurality of second reads corresponds to one of at least the first or the second sample identifier. Obtaining the second data can include storing the second data representing one or more second reads generated during a second read interval in a memory of device of the secondary analysis unit after the second data is generated by the sequencing device. The memory device of the secondary analysis unit may be a memory unit that is accessible by an integrated circuit of the secondary analysis unit configured to perform secondary analysis operations. The integrated circuit can include one or more programmable circuits, one or more ASICs, or a combination thereof. In some implementation, at least a portion of the second data is obtained while another portion of the second data is being generated by the nucleic acid sequencing device. That is, data representing a second set of one or more reads can be obtained and stored in a memory of the sequencing device while one or more other second reads are generated by the nucleic acid sequencing device during the second read interval.

Each read of the plurality of second reads may be comprised of an ordered sequence of nucleotides. In some implementations, the ordered sequence of nucleotides can correspond to nucleotides of a second end of the nucleic acid fragment that is opposite the first end of the nucleic acid fragment. The nucleic acid fragment may be have been clonally amplified to facilitate sequencing and, in such implementations, the ordered sequence of nucleotides may be determined by analyzing plurality of clones of the nucleic acid fragment to generated the nucleotides of the read. Each second sample identifier of each second read, generated in advance of the second read interval, corresponds respectively to a particular identifier of the second read. The second sample identifier can be used by the sequencing system to determine a sample associated with any particular second read. In some implementations, the data identifying the sample can include a barcode.

The sequencing system can continue execution of the process 600 by performing 660 secondary analysis on the obtained second data. In some implementations, the sequencing system can proceed to stage 660 after completion of stage 650. In the context of process 600, this may occur while still achieving at least some of benefits of the present disclosure such as expedited tertiary analysis because sequencing quality could be evaluated during the first read interval in stage 640 and reduction of downtime for the nucleic acid sequencer. However, the present disclosure is not so limited. Instead, in some implementations, the sequencing system can parallelize the secondary analysis of the second reads in the same manner as secondary analysis of the first reads was parallelized with the first read interval.

In some implementations, the sequencing system can rely on the secondary analysis results of mapping and aligning, variant calling, or both, of the organized groups of first reads performed at stage 640 while the first data was being obtained during the first read interval. In other implementations, these initial secondary analysis results related to the organized groups of first reads performed at stage 640 can be discarded after they are evaluated to determine quality of the first read interval. In such instances, the sequencing system can initiate a second iteration of the secondary analysis of the organized groups of first reads either before or after secondary analysis of the organized groups of second reads at stage 660 is completed.

Figure 7:
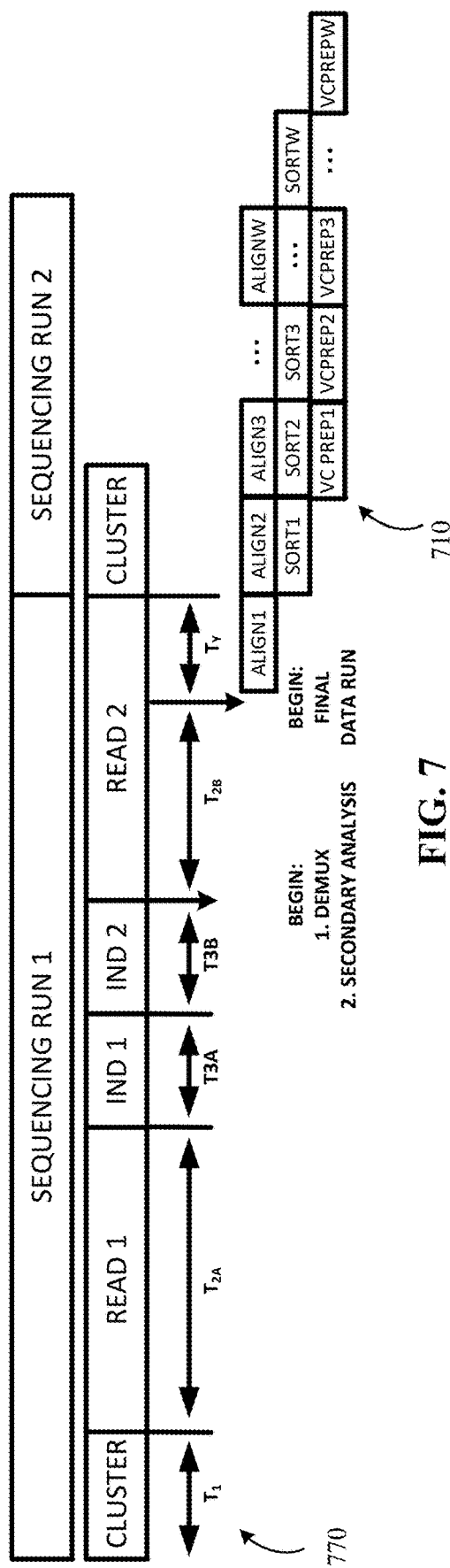
FIG. 7 is an example of a workflow diagram describing a workflow of operations executed during a process for performing incremental secondary analysis using a secondary analysis unit.

FIG. 7 is an example of a workflow diagram 770 describing a workflow of operations executed during a process for performing incremental secondary analysis using a secondary analysis unit. The workflow diagram 770 is the same as the workflow diagram 370 shown in FIG. 3. However, in FIG. 7, a sequence 710 of additional operations that are to be performed during a final data run have been overlayed on top of the workflow diagram 770.

In some implementations, a final data run can include secondary analysis, or other additional processing, that will yield secondary analysis results having a threshold level of confidence. In conventional sequencing systems, a final data run cannot be achieved by conventional sequencing systems until both the first read interval and second read interval have been completed. Moreover, such conventional systems also have sequencer downtime between end of a first sequencing run and a start of a second sequencing run, as shown in FIG. 1A. Though example implementations that uses a threshold level of confidence is described, other implementations can be employed that do not utilize such thresholds.

In the example of FIG. 7, a sequencing system such as the sequencing system of FIG. 3 or 5 can be configured to begin a final data run at time TY before the conclusion of the second read interval. The time TY can be, for example, a predetermined number of one or more sequencing cycles from the end of the second read interval, where a cycle refers to the time required to generate a single nucleic acid from a read. In some implementations, the nucleic acid sequencer can be configured to detect when it is a predetermined number of sequencing cycles from the end of the second read interval "Read 2," and initiate performance of the secondary analysis on one or more first reads generated during the first read interval "Read 1." The first reads can include one or more organized sets of reads that have been previously demultiplexed at the conclusion of time T3B in workflow of FIG. 7. Initiating performance of secondary analysis can include, for example, instructing a secondary analysis unit to perform mapping and aligning, variant calling of mapped and aligned reads, or both.

Once initiated, the secondary analysis unit can continue to perform secondary analysis operations of reads generating during the first and second read intervals of the first sequencing run until the triggered secondary analysis operations are completed. As shown in FIG. 7, execution of the secondary analysis operations using the secondary analysis unit can begin during a first sequencing run and continue executing during a second sequencing run that begins after completion of the first sequencing run. The secondary analysis operations on the reads generated during the first sequencing run will complete during the second sequencing run. This parallelization of secondary analysis corresponding to the first sequencing run with the operations of the second sequencing run thus enables a nucleic acid sequencer to continue sequencing runs, with little to no sequencer downtime, thus increasing reagent consumption and revenue derived therefrom. The operations of the second sequencing run that overlap with the secondary analysis of the first sequencing run can include, but are not limited to, the setup, clustering, or primary analysis of the second sequencing run.

In the example of FIG. 7, the parallelization of secondary analysis of the first sequencing run and operations of the second sequencing run is not being performed to evaluate the quality of the reads generated by the nucleic acid sequencer in an effort to determine whether the second read interval should continue. Instead, the parallelization of secondary analysis and operations of the second sequencing run is being performed as part of the final data run, making the final result data suitable for use in subsequent operations such as during tertiary analysis.

Figure 8:
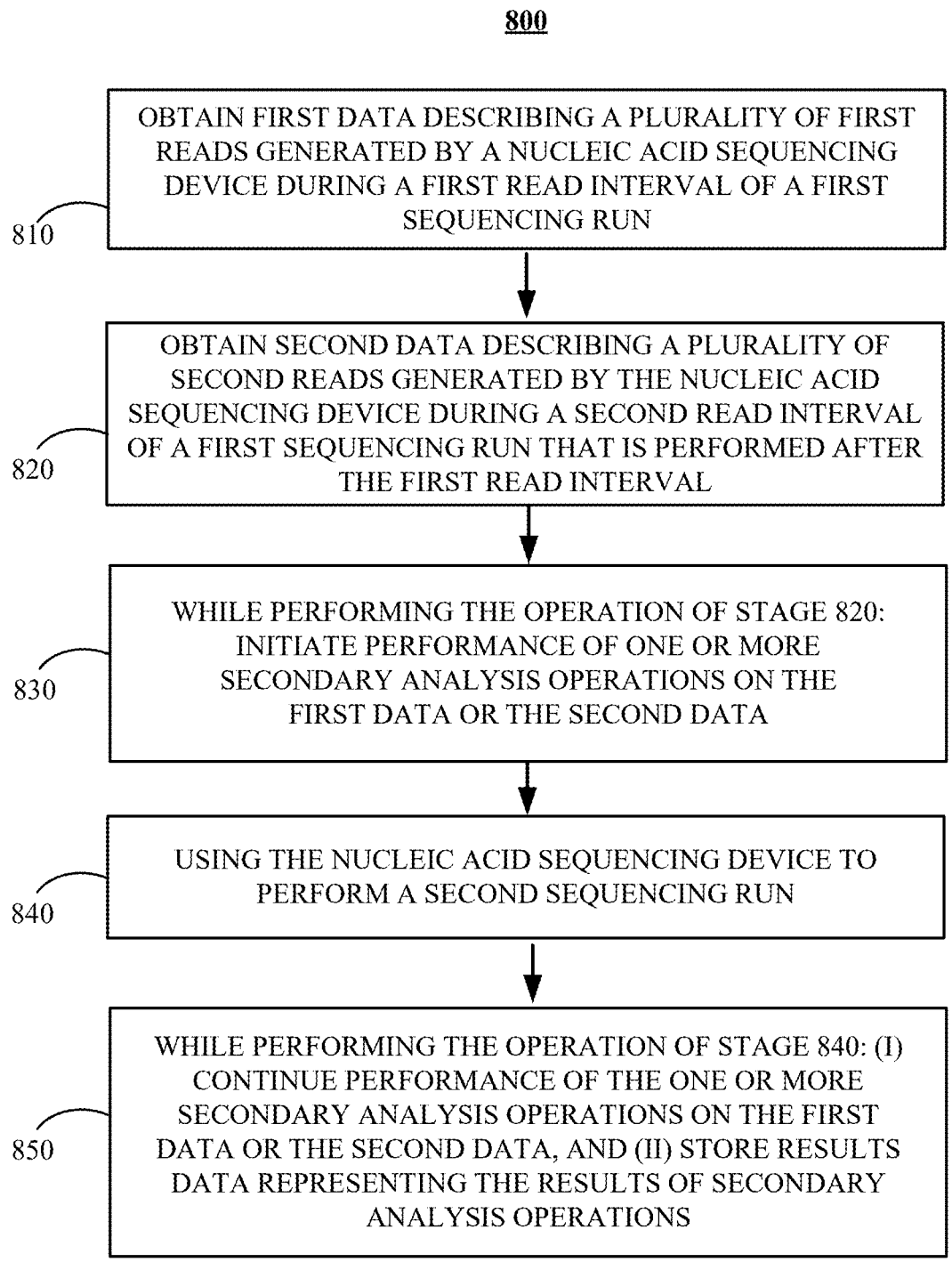
FIG. 8 is a flowchart of an example of a process for performing incremental secondary analysis in accordance with the workflow diagram of FIG. 7.

FIG. 8 is a flowchart of an example of a process 800 for performing incremental secondary analysis in accordance with the workflow diagram of FIG. 7. In general, the obtaining first data describing a plurality of first reads generated by a nucleic acid sequencing device during a first read interval of a first sequencing run (810), obtaining second data describing a plurality of second reads generated by the nucleic acid sequencing device during a second read interval of a first sequencing run that is performed after the first read interval (820), while obtaining at least a portion of the second data at stage 820, initiating performance of one or more secondary analysis operations on at least the first data or second data (830), using the nucleic acid sequencing device to perform a second sequencing run (840), and while using the nucleic acid sequencing device to perform a second sequencing run at stage 840, (I) continuing performance of the one or more secondary analysis operations on the first data or the second data, and (II) storing results data representing the results of the secondary analysis operations (850). For convenience, and without limitation, these stages will be described in more detail below as being performed by a sequencing system such as system 100, 300, or 500 of FIGS. 1A, 3, or 5, respectively.

A sequencing system can begin performance of the process 800, at stage 810, by obtaining first data describing a plurality of first reads generated by a nucleic acid sequencing device during a first read interval of a first sequencing run. Obtaining the first data can include storing the first data describing the plurality of first reads in a memory device such as a memory device of a secondary analysis unit after the first data is generated by the nucleic acid sequencing device. The memory device of the secondary analysis unit may be a memory unit that is accessible by an integrated circuit of the secondary analysis unit configured to perform secondary analysis operations. The integrated circuit can include one or more programmable circuits, one or more ASICs, or a combination thereof.

Each read of the plurality of first reads may be comprised of an ordered sequence of nucleotides. In some implementations, the ordered sequence of nucleotides can correspond to nucleotides of a first end of a nucleic acid fragment. The nucleic acid fragment may be have been clonally amplified to facilitate sequencing and, in such implementations, the ordered sequence of nucleotides may be determined by analyzing plurality of clones of the nucleic acid fragment to generated the nucleotides of the read. The nucleic acid sequencing device can include any nucleic acid sequencing device including a DNA sequencer or an RNA sequencer. The first sequencing run can include a complete performance of primary analysis of one or more biological samples by the nucleic acid sequencing device. An example of the stages of a complete first sequencing run is shown in FIG. 7 and includes a clustering stage, first read interval, and a second read interval. In some implementations, such as the one shown in FIG. 7, primary analysis can also include one or more indexing stages.

The sequencing system can continue performance of the process 800, at stage 820, by obtaining second data describing a plurality of second reads generated by the nucleic acid sequencing device during a second read interval of a first sequencing run that is performed after the first read interval.

Obtaining the second data can include storing the second data representing the plurality of second reads in a memory of a secondary analysis unit after the second data is generated by the sequencing device. The memory device of the secondary analysis unit may be a memory unit that is accessible by an integrated circuit of the secondary analysis unit configured to perform secondary analysis operations. The integrated circuit can include one or more programmable circuits, one or more ASICs, or a combination thereof. In some implementation, at least a portion of the second data is obtained while another portion of the second data is being generated by the nucleic acid sequencing device. Each read of the plurality of second reads may be comprised of an ordered sequence of nucleotides. In some implementations, the ordered sequence of nucleotides can correspond to nucleotides of a second end of the nucleic acid fragment that is opposite of the first end of the nucleic acid fragment. The nucleic acid fragment may be have been clonally amplified to facilitate sequencing and, in such implementations, the ordered sequence of nucleotides may be determined by analyzing plurality of clones of the nucleic acid fragment to generated the nucleotides of the read.

While obtaining at least a portion of the second data at stage 820, the sequencing system can continue performance of the process 800, at stage 830, by initiating performance of one or more secondary analysis operations on the first data or second data. Initiating performance of one or more secondary analysis operations can include dynamically configuring a programmable circuit to include hardwired logic to perform a secondary analysis operation, and then performing at least one secondary analysis operation for one or more reads generated during the first sequencing run. For example, the sequencing system can dynamically configure a programmable circuit as a mapping and aligning unit, and then use the hardwired logic of mapping and aligning unit to perform mapping and aligning of at least one read generated during the first sequencing run. In other implementations, initiating performance of one or more secondary analysis operations can include instructing an ASIC to execute hardwired digital logic to perform the secondary analysis operation on one or more reads generated during the first sequencing run.

In some implementations, such as when multiple samples were sequenced during the first sequencing run, the first reads or the second reads may need to be organized into demultiplexed groups prior to mapping and aligning. In such implementations, at least a portion of the organization of the first read, the second reads, or both, can also be performed during stage 820.

The sequencing system can continue performance of the process 800, at stage 840, by using the nucleic acid sequencing device to perform a second sequencing run. The second sequencing run can includes a complete performance of primary analysis of one or more biological samples by the nucleic acid sequencing device. In some implementations, the second sequencing run can sequence one or more different biological samples than those biological samples sequenced during the first sequencing run. The second sequencing run can include a clustering stage, first read interval, and a second read interval. In some implementations, primary analysis can also include one or more indexing stages.

While using the nucleic acid sequencing device to perform a second sequencing run at stage 840, (I) continuing 850 performance of the one or more secondary analysis operations on the first data or the second data, and (II) storing results data representing the results of the secondary analysis operations. Continuing performance of the one or more secondary analysis operations on the first data or the second data generated during stages 810 or 820, respectively, can include continuing performance of secondary analysis on the first and second data until secondary analysis on the first and second data is complete. For example, the hardwired mapping and aligning unit that can be configured at stage 830 during the first sequencing run can continue performing mapping and aligning operations of first reads, second reads, or both, during the second sequencing run until mapping and aligning operations on the first reads, second reads, or both, are complete.

Figure 9:
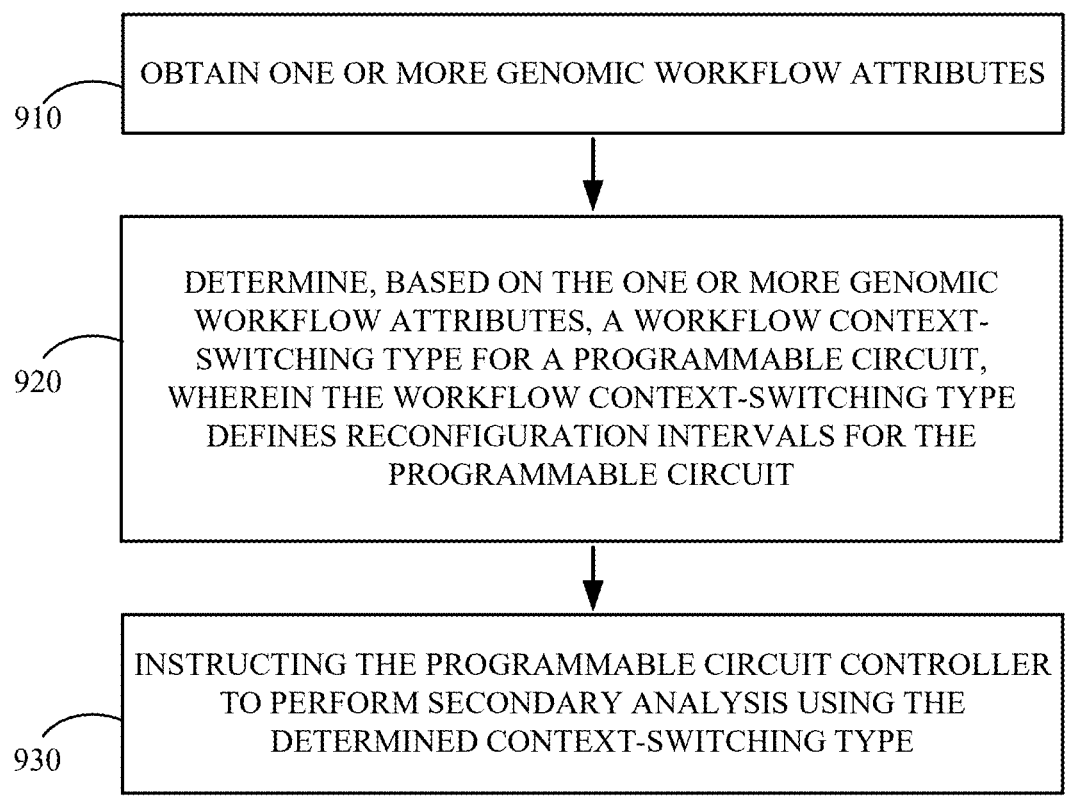
FIG. 9 is flowchart of an example of a process for performing dynamic programmable circuit context-switching.

FIG. 9 is flowchart of an example of a process 900 for performing dynamic programmable circuit context-switching. In general, the process 900 can include obtaining one or more genomic workflow attributes (910), determining, based on the one or more genomic workflow attributes, a workflow context-switching type for a programmable circuit, wherein the workflow context-switching type defines reconfiguration for the programmable circuit (920), and instructing the programmable circuit controller to perform secondary analysis using the determined context-switching type (930). For convenience, and without limitation, these stages will be described in more detail below as being performed by a sequencing system such as system 100, 300, or 500 of FIGS. 1A, 3, or 5, respectively.

A sequencing system can begin execution of the process 900, at stage 910, by obtaining one or more genomic workflow attributes. In some implementations, the one or more workflow attributes can include a workflow identifier that identifies a workflow selected by a user of a nucleic acid sequencer. Genomic workflows can include, for example, a whole genome sequencing workflow, an enrichment workflow, an RNA workflow, an Amplicon workflow, a Single Cell RNA workflow, or the like. Alternatively, or in addition, the one or more workflow attributes may include data describing a number of samples being sequenced by a nucleic acid sequencer. Alternatively, or in addition, the one or more workflow attributes can include a predetermined time threshold for execution of the workflow. Alternatively, or in addition, the one or more workflow attributes can include an amount of available computing resources available to the nucleic acid sequencer.

The sequencing system can continue execution of the process 900, at stage 920, by determining, based on the one or more genomic workflow attributes, a workflow context-switching type for a programmable circuit, wherein the workflow context-switching type defines reconfiguration for the programmable circuit. Determining a workflow context-switching type can include selecting a particular workflow context-switching type from a plurality of context-switching types based on the one or more workflow attributes.

A context-switching type defines how a programmable circuit will be dynamically reconfigured at runtime. By way of example, a first programmable circuit context can include the programmable circuit interlacing alignment and variant calling operations. In such implementations, the programmable circuit can be configured as a mapping and aligning unit to align reads corresponding to a first sample to a reference sequence, dynamically reconfigured as a variant calling unit to perform variant calling operations on the reads corresponding to the first aligned sample, dynamically reconfigured to map and align a reads corresponding to a second sample to the reference sequence, dynamically reconfigured as a variant calling unit to perform variant calling operations on the reads corresponding to a second aligned sample, and so on. In this context, the programmable circuit can dynamically switch back and forth between mapping and aligning and variant calling operations. This first programmable circuit context is preferred when there is only one sample or a small number of samples.

By way of another example, a second programmable circuit context can include the programmable circuit performing all necessary alignments and then performing all necessary variant calling operations on the aligned reads. In such implementations, the programmable circuit can be configured as a mapping and aligning unit and align a first sample, align a second sample, align a third, etc., until all samples are aligned and then dynamically reconfigured as a variant calling unit to perform variant calling operations on the first aligned sample, perform variant calling operations on the second aligned sample, perform variant calling operations on the third aligned sample, etc. Because context-switching is an expensive computing function, this second programmable circuit context can be selected when a workflow has a larger number of samples.

In some implementations, the sequencing system can determine between the aforementioned context-switching types in a number of ways. For example, in some implementations, the sequencing system can obtain data such as a workflow identifier that is indicative of a workflow selection by a user of a nucleic acid sequencer. In some implementations, the sequencing system can be programmed to automatically select a particular context-switching type that is logically related to the obtained workflow identifier. A logical relationship can include, for example, a one-to-one mapping between the workflow identifier and context-switching type.

Alternatively, or in addition, the sequencing system can determine between the aforementioned context-switching types based on a number of samples. For example, a predetermined threshold number of samples can be established. Then, if the nucleic acid sequencer determines that a particular workflow has more than a threshold number of samples, then the nucleic acid sequencer can select second programmable context. Alternatively, if the nucleic acid sequence determines that the number of samples does not exceed the threshold number of samples, then the nucleic acid sequencer can select the first programmable context.

Alternatively, or in addition, the sequencing system can determine between the aforementioned context-switching types based on an estimated secondary analysis runtime. For example, a nucleic acid sequencer can be programmed to analyze data describing a received workflow, and estimate an estimated secondary analysis runtime using a default programmable circuit context, where the default programmable circuit context is the first programmable circuit context. In such implementations, if the estimated secondary analysis runtime is less than a predetermined threshold time, then the nucleic acid sequencer can select the first programmable circuit context. Alternatively, if the estimated secondary analysis runtime is more than a predetermined threshold time, then the nucleic acid sequencer can select the second programmable circuit context.

These aforementioned implementations are mere examples of programmable circuit context types and context-switching that can be employed by the present disclosure. None of these examples should be viewed as limiting the scope of the present disclosure. Instead, other programmable circuit context types and context-switching types falls within the scope of the present disclosure.

The sequencing system can continue performance of the process 900, at stage 930, by instructing the programmable circuit controller to perform secondary analysis using the determined context-switching type. The programmable circuit controller can include software, hardware, or combination of both, that configures the programmable logic of the programmable circuit. Based on the received instructions, the programmable circuit controller can dynamically configure the programmable circuit to include hardwired digital logic that is configured to perform the context-switching type identified by the instructions.

Figure 10:
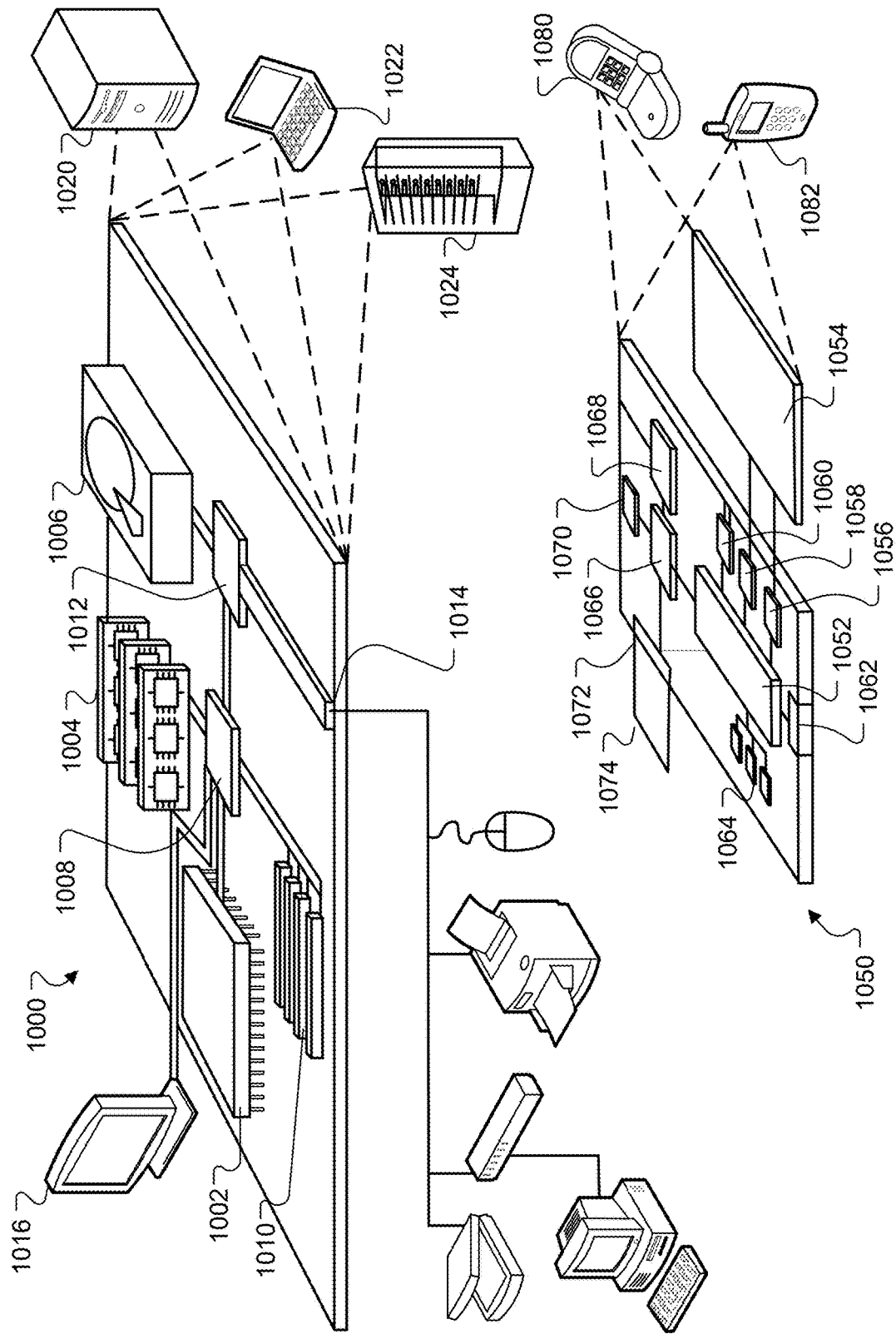
FIG. 10 is a block diagram of an example of system components that can be used to implement a system for performing incremental secondary analysis.

FIG. 10 is a block diagram of an example of system components that can be used to implement a system for performing incremental secondary analysis.

The computing device 1000 is intended to represent various forms of digital computers, such as laptops, desktops, workstations, personal digital assistants, servers, blade servers, mainframes, and other appropriate computers. In some implementations, the computing device 1000 can be a nucleic acid sequencer such as the nucleic acid sequencer of FIG. 1, 3, or 5. The mobile computing device 1050 is intended to represent various forms of mobile devices, such as personal digital assistants, cellular telephones, smartphones, mobile embedded radio systems, radio diagnostic computing devices, and other similar computing devices. The components shown here, their connections and relationships, and their functions, are meant to be examples only, and are not meant to be limiting.

The computing device 1000 includes a processor 1002, a memory 1004, a storage device 1006, a high-speed interface 1008 connecting to the memory 1004 and multiple high-speed expansion ports 1010, and a low-speed interface 1012 connecting to a low-speed expansion port 1014 and the storage device 1006. Each of the processor 1002, the memory 1004, the storage device 1006, the high-speed interface 1008, the high-speed expansion ports 1010, and the low-speed interface 1012, are interconnected using various busses, and may be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as a display 1016 coupled to the high-speed interface 1008. In other implementations, multiple processors and/or multiple buses may be used, as appropriate, along with multiple memories and types of memory. In addition, multiple computing devices may be connected, with each device providing portions of the operations (e.g., as a server bank, a group of blade servers, or a multi-processor system). In some implementations, the processor 1002 is a single threaded processor. In some implementations, the processor 1002 is a multi-threaded processor. In some implementations, the processor 1002 is a quantum computer.

The memory 1004 stores information within the computing device 1000. In some implementations, the memory 1004 is a volatile memory unit or units. In some implementations, the memory 1004 is a non-volatile memory unit or units. The memory 1004 may also be another form of computer-readable medium, such as a magnetic or optical disk.

The storage device 1006 is capable of providing mass storage for the computing device 1000. In some implementations, the storage device 1006 may be or include a computer-readable medium, such as a floppy disk device, a hard disk device, an optical disk device, or a tape device, a flash memory or other similar solid-state memory device, or an array of devices, including devices in a storage area network or other configurations. Instructions can be stored in an information carrier. The instructions, when executed by one or more processing devices (for example, processor 1002), perform one or more methods, such as those described above. The instructions can also be stored by one or more storage devices such as computer- or machine readable mediums (for example, the memory 1004, the storage device 1006, or memory on the processor 1002). The high-speed interface 1008 manages bandwidth-intensive operations for the computing device 1000, while the low-speed interface 1012 manages lower bandwidth-intensive operations. Such allocation of functions is an example only. In some implementations, the high speed interface 1008 is coupled to the memory 1004, the display 1016 (e.g., through a graphics processor or accelerator), and to the high-speed expansion ports 1010, which may accept various expansion cards (not shown). In the implementation, the low-speed interface 1012 is coupled to the storage device 1006 and the low-speed expansion port 1014. The low-speed expansion port 1014, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1000 may be implemented in a number of different forms, as shown in the figure. For example, it may be implemented as a standard server 1020, or multiple times in a group of such servers. In addition, it may be implemented in a personal computer such as a laptop computer 1022. It may also be implemented as part of a rack server system 1024. Alternatively, components from the computing device 1000 may be combined with other components in a mobile device, such as a mobile computing device 1050. Each of such devices may include one or more of the computing device 1000 and the mobile computing device 1050, and an entire system may be made up of multiple computing devices communicating with each other.

The mobile computing device 1050 includes a processor 1052, a memory 1064, an input/output device such as a display 1054, a communication interface 1066, and a transceiver 1068, among other components. The mobile computing device 1050 may also be provided with a storage device, such as a micro-drive or other device, to provide additional storage. Each of the processor 1052, the memory 1064, the display 1054, the communication interface 1066, and the transceiver 1068, are interconnected using various buses, and several of the components may be mounted on a common motherboard or in other manners as appropriate.

The processor 1052 can execute instructions within the mobile computing device 1050, including instructions stored in the memory 1064. The processor 1052 may be implemented as a chipset of chips that include separate and multiple analog and digital processors. The processor 1052 may provide, for example, for coordination of the other components of the mobile computing device 1050, such as control of user interfaces, applications run by the mobile computing device 1050, and wireless communication by the mobile computing device 1050.

The processor 1052 may communicate with a user through a control interface 1058 and a display interface 1056 coupled to the display 1054. The display 1054 may be, for example, a TFT (Thin-Film-Transistor Liquid Crystal Display) display or an OLED (Organic Light Emitting Diode) display, or other appropriate display technology. The display interface 1056 may include appropriate circuitry for driving the display 1054 to present graphical and other information to a user. The control interface 1058 may receive commands from a user and convert them for submission to the processor 1052. In addition, an external interface 1062 may provide communication with the processor 1052, so as to enable near area communication of the mobile computing device 1050 with other devices. The external interface 1062 may provide, for example, for wired communication in some implementations, or for wireless communication in other implementations, and multiple interfaces may also be used.

The memory 1064 stores information within the mobile computing device 1050. The memory 1064 can be implemented as one or more of a computer-readable medium or media, a volatile memory unit or units, or a non-volatile memory unit or units. An expansion memory 1074 may also be provided and connected to the mobile computing device 1050 through an expansion interface 1072, which may include, for example, a SIMM (Single In Line Memory Module) card interface. The expansion memory 1074 may provide extra storage space for the mobile computing device 1050, or may also store applications or other information for the mobile computing device 1050. Specifically, the expansion memory 1074 may include instructions to carry out or supplement the processes described above, and may include secure information also. Thus, for example, the expansion memory 1074 may be provide as a security module for the mobile computing device 1050, and may be programmed with instructions that permit secure use of the mobile computing device 1050. In addition, secure applications may be provided via the SIMM cards, along with additional information, such as placing identifying information on the SIMM card in a non-hackable manner.

The memory may include, for example, flash memory and/or NVRAM memory (nonvolatile random access memory), as discussed below. In some implementations, instructions are stored in an information carrier such that the instructions, when executed by one or more processing devices (for example, processor 1052), perform one or more methods, such as those described above. The instructions can also be stored by one or more storage devices, such as one or more computer- or machine-readable mediums (for example, the memory 1064, the expansion memory 1074, or memory on the processor 1052). In some implementations, the instructions can be received in a propagated signal, for example, over the transceiver 1068 or the external interface 1062.

The mobile computing device 1050 may communicate wirelessly through the communication interface 1066, which may include digital signal processing circuitry in some cases. The communication interface 1066 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), LTE, 5G/6G cellular, among others. Such communication may occur, for example, through the transceiver 1068 using a radio frequency. In addition, short-range communication may occur, such as using a Bluetooth, Wi-Fi, or other such transceiver (not shown). In addition, a GPS (Global Positioning System) receiver module 1070 may provide additional navigation- and location-related wireless data to the mobile computing device 1050, which may be used as appropriate by applications running on the mobile computing device 1050.

The mobile computing device 1050 may also communicate audibly using an audio codec 1060, which may receive spoken information from a user and convert it to usable digital information. The audio codec 1060 may likewise generate audible sound for a user, such as through a speaker, e.g., in a handset of the mobile computing device 1050. Such sound may include sound from voice telephone calls, may include recorded sound (e.g., voice messages, music files, among others) and may also include sound generated by applications operating on the mobile computing device 1050.

The mobile computing device 1050 may be implemented in a number of different forms, as shown in the figure. For example, it may be implemented as a cellular telephone 1080. It may also be implemented as part of a smart-phone 1082, personal digital assistant, or other similar mobile device.

A number of implementations have been described. Nevertheless, it will be understood that various modifications may be made without departing from the spirit and scope of the disclosure. For example, various forms of the flows shown above may be used, with steps re-ordered, added, or removed.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The terms "data processing apparatus" can encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where a specific file format such is mentioned, other file types or formats may be substituted. For example, an HTML file may be replaced by an XML, JSON, plain text, or other types of files. Moreover, where a particular data structure such as a table or hash table is mentioned, other data structures (such as spreadsheets, relational databases, or structured files) may be used in place of the mentioned data structure.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Particular embodiments of the invention have been described. Other embodiments are within the scope of the following claims. For example, the steps recited in the claims can be performed in a different order and still achieve desirable results.

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

The invention claimed is:

1. A method for performing incremental secondary analysis of nucleic acid sequence reads, the method comprising:
   (i) obtaining, by one or more processors of a nucleic acid sequencing device, first data describing a plurality of first reads generated by the nucleic acid sequencing device during a first read interval, wherein each read of the first reads represents a first ordered sequence of nucleotides
   (ii) obtaining, by one or more processors of the nucleic acid sequencing device, second data describing a plurality of second reads generated by the nucleic acid sequencing device during a second read interval that is performed after the first read interval, wherein each read of the second reads represents a second ordered sequence of nucleotides, wherein while the second data is being obtained, the method further comprises:
      (a) providing, by one or more processors of the nucleic acid sequencing device, the first data as an input to a mapping and alignment engine;
      (b) receiving, by one or more processors of the nucleic acid sequencing device and from the mapping and alignment engine alignment results that indicate a quality of an alignment of the first data;
      (c) determining, by one or more processors of the nucleic acid sequencing device and based on the received alignment results of the first data, that the nucleic acid sequencing device is to terminate operations that obtain the second data; and
      (d) causing, by one or more processors of the nucleic acid sequencing device, the nucleic acid sequencing device to terminate operations that obtain the second data.

2. The method of claim 1, wherein the mapping and alignment engine is included within the nucleic acid sequencing device.

3. The method of claim 1,
wherein one or more of the first reads includes data representing a first sample identifier, and
wherein one or more of the second reads includes data representing a second sample identifier.

4. The method of claim 3, further comprising:
while the second data is being obtained:
   organizing, by one or more processors of the nucleic acid sequencing device, the one or more first reads into respective groups based on at least a first sample identifier or a second sample identifier; and
   generating, by one or more processors of the nucleic acid sequencing device, organization statistics, the organization statistics indicating a number of first reads corresponding to each sample identifier.

5. The method of claim 1, the method further comprising:
providing, by one or more processors of the nucleic acid sequencing device, output data that represents the received alignment results of the first data before or while aligning the second portion of the cluster of reads.

6. The method of claim 1, the method further comprising:
causing, by one or more processors of the nucleic acid sequencing device, the mapping and alignment engine to begin a subsequent alignment of the data representing the first plurality of reads to the reference sequence.

7. The method of claim 1, the method further comprising:
while obtaining the second data, causing, by one or more processors of the nucleic acid sequencing device, a secondary analysis engine to determine a set of likely variants for the first data representing the first plurality of reads that was aligned to the reference sequence.

8. The method of claim 1, wherein the at least a portion of the second data representing the second plurality of reads is aligned while at least a different portion of second data representing the second plurality of reads is being obtained.

9. The method of claim 1, wherein the mapping and alignment engine is instructed to begin alignment of the second data representing the second plurality of reads a predetermined number of sequencing cycles before the second data is completely obtained.

10. The method of claim 1, wherein the mapping and alignment engine is implemented using a field programmable gate array (FPGA).

11. The method of claim 1, wherein the mapping and alignment engine is implemented using an Application Specific Integrated Circuit (ASIC).

12. The method of claim 1, wherein the mapping and alignment engine is implemented by using one or more computers to execute software instructions.

13. A system for performing incremental secondary analysis of nucleic acid sequence reads, the system comprising:
a nucleic acid sequencing device; and
one or more memory devices storing instructions that, when executed by one or more processors of the nucleic acid sequencing device, cause the nucleic acid sequencing device to perform operations, the operations comprising:
(i) obtaining, by the one or more processors of the nucleic acid sequencing device, first data describing a plurality of first reads generated by the nucleic acid sequencing device during a first read interval, wherein each read of the first reads represents a first ordered sequence of nucleotides;
(ii) obtaining, by the one or more processors of the nucleic acid sequencing device, second data describing a plurality of second reads generated by the nucleic acid sequencing device during a second read interval that is performed after the first read interval, wherein each read of the second reads represents a second ordered sequence of nucleotides, wherein while the second data is being obtained, the operations further comprising:
(a) providing, by the one or more processors of the nucleic acid sequencing device, the first data as an input to a mapping and alignment engine;
(b) receiving, by the one or more processors of the nucleic acid sequencing device and from the mapping and alignment engine, alignment results that indicate a quality of an alignment of the first data;
(c) determining, by the one or more processors of the nucleic acid sequencing device and based on the received alignment results of the first data, that the nucleic acid sequencing device is to terminate operations that obtain the second data; and
(d) causing, by the one or more processors of the nucleic acid sequencing device, the nucleic acid sequencing device to terminate operations that obtain the second data.

14. The system of claim 13, wherein the mapping and alignment engine is included within the nucleic acid sequencing device.

15. The system of claim 13,
wherein one or more of the first reads includes data representing a first sample identifier, and
wherein one or more of the second reads includes data representing a second sample identifier.

16. The system of claim 15, the operations further comprising:
while the second data is being obtained:
organizing, by the one or more processors of the nucleic acid sequencing device, the one or more first reads into respective groups based on at least a first sample identifier or a second sample identifier; and
generating, by one or more processors of the nucleic acid sequencing device, organization statistics, the organization statistics indicating a number of first reads corresponding to each sample identifier.

17. The system of claim 13, the operations further comprising:
providing, by the one or more processors of the nucleic acid sequencing device, output data that represents the received alignment results of the first data before or while aligning the second portion of the cluster of reads.

18. The system of claim 13, the operations further comprising:
causing, by the one or more processors of the nucleic acid sequencing device, the mapping and alignment engine to begin a subsequent alignment of the data representing the first plurality of reads to the reference sequence.

19. The system of claim 13, the operations further comprising:
while obtaining the second data, causing, by the one or more processors of the nucleic acid sequencing device, a secondary analysis engine to determine a set of likely variants for the first data representing the first plurality of reads that was aligned to the reference sequence.

20. The system of claim 13, wherein the at least a portion of the second data representing the second plurality of reads is aligned while at least a different portion of second data representing the second plurality of reads is being obtained.

21. The system of claim 13, wherein the mapping and alignment engine is instructed to begin alignment of the second data representing the second plurality of reads a predetermined number of sequencing cycles before the second data is completely obtained.

22. The system of claim 13, wherein the mapping and alignment engine is implemented using a field programmable gate array (FPGA).

23. The system of claim 13, wherein the mapping and alignment engine is implemented using an Application Specific Integrated Circuit (ASIC).

24. The system of claim 13, wherein the mapping and alignment engine is implemented by using one or more computers to execute software instructions.

25. A non-transitory computer-readable storage medium storing instructions that, when executed by one or more computers, causes the one or more processors of a nucleic acid sequencing device to perform operations, the operations comprising:
(i) obtaining first data describing a plurality of first reads generated by a nucleic acid sequencing device during a first read interval, wherein each read of the first reads represents a first ordered sequence of nucleotides
(ii) obtaining second data describing a plurality of second reads generated by the nucleic acid sequencing device during a second read interval that is performed after the first read interval, wherein each read of the second reads represents a second ordered sequence of nucleotides, wherein while the second data is being obtained, the operations further comprising:
(a) providing, by the nucleic acid sequencing device, the first data as an input to a mapping and alignment engine;
(b) receiving, from the mapping and alignment engine, alignment results that indicate a quality of an alignment of the first data;
(c) determining, based on the received alignment results, whether to terminate sequencing operations; and
(d) causing the nucleic acid sequencing device to terminate operations that obtain the second data.

26. The computer-readable storage medium of claim 25, wherein one or more of the first reads includes data representing a first sample identifier, and
wherein one or more of the second reads includes data representing a second sample identifier.

27. The computer-readable storage medium of claim 26, the operations comprising:
while the second data is being obtained:
organizing the one or more first reads into respective groups based on at least a first sample identifier or a second sample identifier; and
generating organization statistics, the organization statistics indicating a number of first reads corresponding to each sample identifier.

28. The computer-readable storage medium of claim 25, the operations further comprising:
providing output data that represents the received alignment results of the first data before or while aligning the second portion of the cluster of reads.

29. The computer-readable storage medium of claim 25, the operations further comprising:
causing the mapping and alignment engine to begin a subsequent alignment of the data representing the first plurality of reads to the reference sequence.

30. The computer-readable storage medium of claim 25, the operations further comprising:
while obtaining the second data, causing a secondary analysis engine to determine a set of likely variants for the first data representing the first plurality of reads that was aligned to the reference sequence.

31. The computer-readable storage medium of claim 25, wherein the at least a portion of the second data representing the second plurality of reads is aligned while at least a different portion of second data representing the second plurality of reads is being obtained.

32. The computer-readable storage medium of claim 25, wherein the mapping and alignment engine is instructed to begin alignment of the second data representing the second plurality of reads a predetermined number of sequencing cycles before the second data is completely obtained.

33. The non-transitory computer-readable storage medium of claim 25, wherein the mapping and alignment engine is implemented using a field programmable gate array (FPGA).

34. The non-transitory computer-readable storage medium of claim 25, wherein the mapping and alignment engine is implemented using an Application Specific Integrated Circuit (ASIC).

35. The non-transitory computer-readable storage medium of claim 25, wherein the mapping and alignment engine is implemented by using one or more computers to execute software instructions.

* * * * *